United States Patent
Sakairi et al.

(10) Patent No.: US 11,443,851 B2
(45) Date of Patent: Sep. 13, 2022

(54) CANCER TEST SYSTEM AND METHOD FOR ASSESSING CANCER TEST

(71) Applicant: Hirotsu Bio Science Inc., Tokyo (JP)

(72) Inventors: Minoru Sakairi, Tokyo (JP); Masakazu Sugaya, Tokyo (JP); Koichi Terada, Tokyo (JP); Taku Nakamura, Tokyo (JP); Norihito Kuno, Tokyo (JP)

(73) Assignee: Hirotsu Bio Science Inc.

( * ) Notice: Subject to any disclaimer, the term of this patent is extended or adjusted under 35 U.S.C. 154(b) by 966 days.

(21) Appl. No.: 15/769,682

(22) PCT Filed: Nov. 30, 2015

(86) PCT No.: PCT/JP2015/083586
§ 371 (c)(1),
(2) Date: Apr. 19, 2018

(87) PCT Pub. No.: WO2017/094066
PCT Pub. Date: Jun. 8, 2017

(65) Prior Publication Data
US 2018/0313839 A1    Nov. 1, 2018

(51) Int. Cl.
*G16H 50/20*    (2018.01)
*G01N 33/48*    (2006.01)
(Continued)

(52) U.S. Cl.
CPC ............ *G16H 50/20* (2018.01); *G01N 21/00* (2013.01); *G01N 33/48* (2013.01);
(Continued)

(58) Field of Classification Search
CPC .. G16H 50/20; G01N 33/48; G01N 33/57488; G01N 2333/4353; G01N 21/00;
(Continued)

(56) References Cited

U.S. PATENT DOCUMENTS

| 5,023,173 A | 6/1991 | Horwitz et al. |
| 2005/0051723 A1* | 3/2005 | Neagle ................ G01N 21/253 250/306 |
| 2017/0016906 A1* | 1/2017 | Hirotsu ............ G01N 33/57488 |

FOREIGN PATENT DOCUMENTS

| JP | 2-501109 A | 4/1990 |
| JP | 2009-25349 A | 2/2009 |

(Continued)

OTHER PUBLICATIONS

International Search Report (PCT/ISA/210) issued in PCT Application No. PCT/JP2015/083586 dated Feb. 16, 2016 with English-language translation (five (5) pages).
(Continued)

*Primary Examiner* — Rebecca M Fritchman
(74) *Attorney, Agent, or Firm* — Harness, Dickey & Pierce, P.L.C.

(57) ABSTRACT

In order to determine, in a cancer test using nematodes, whether or not the nematodes used in the cancer test are adequate, the present invention is characterized in that after a plate on which a urine from a subject and the nematode are set is placed, a cancer test apparatus performs imaging for quality assay of the nematode during the initial two minutes; an analysis apparatus determines a quality of the nematode using the imaging result; after taxis of the nematode is completed, the cancer test apparatus performs imaging for cancer test assay by the nematode; and the analysis apparatus determines the presence or absence of a cancer in the subject using the imaging result.

9 Claims, 21 Drawing Sheets

(51) Int. Cl.
*G01N 21/00* (2006.01)
*G01N 33/574* (2006.01)
*G01N 33/50* (2006.01)

(52) U.S. Cl.
CPC ..... *G01N 33/5029* (2013.01); *G01N 33/5085* (2013.01); *G01N 33/574* (2013.01); *G01N 33/57488* (2013.01); *G01N 2333/4353* (2013.01)

(58) Field of Classification Search
CPC ............ G01N 33/574; G01N 33/5085; G01N 33/5029
See application file for complete search history.

(56) References Cited

FOREIGN PATENT DOCUMENTS

WO    WO 2015/088039 A1    6/2015
WO    WO-2015088039 A1 *    6/2015    ........... C12Q 1/6888

OTHER PUBLICATIONS

Japanese-language Written Opinion (PCT/ISA/237) issued in PCT Application No. PCT/JP2015/083586 dated Feb. 16, 2016 (three (3) pages).

* cited by examiner

[FIG. 1]
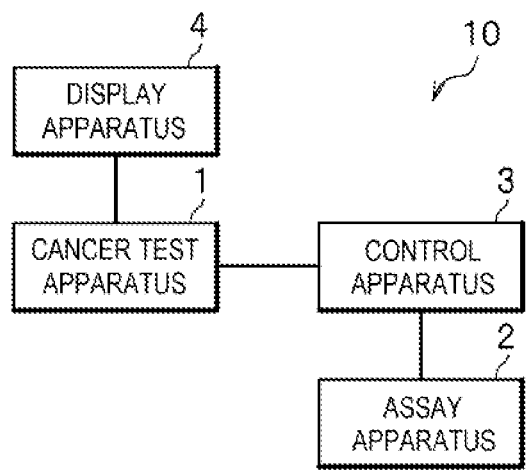
[FIG. 2]
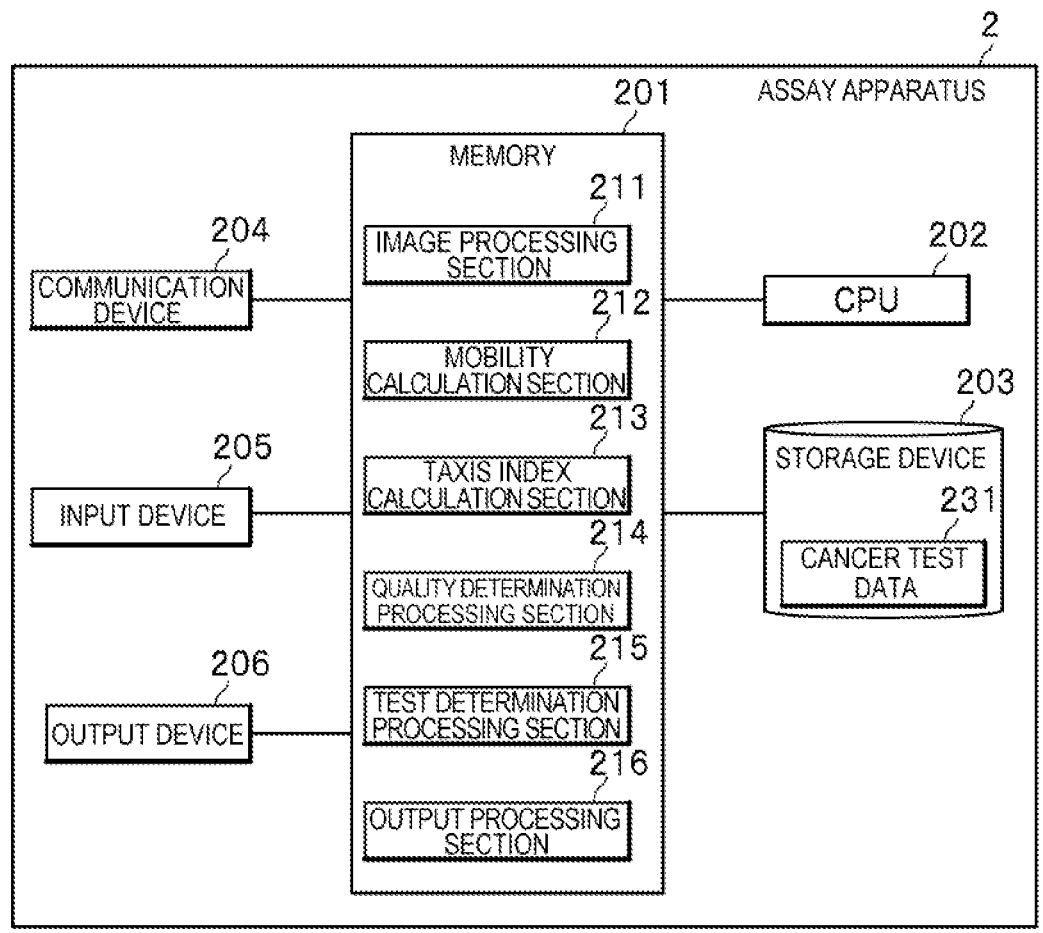

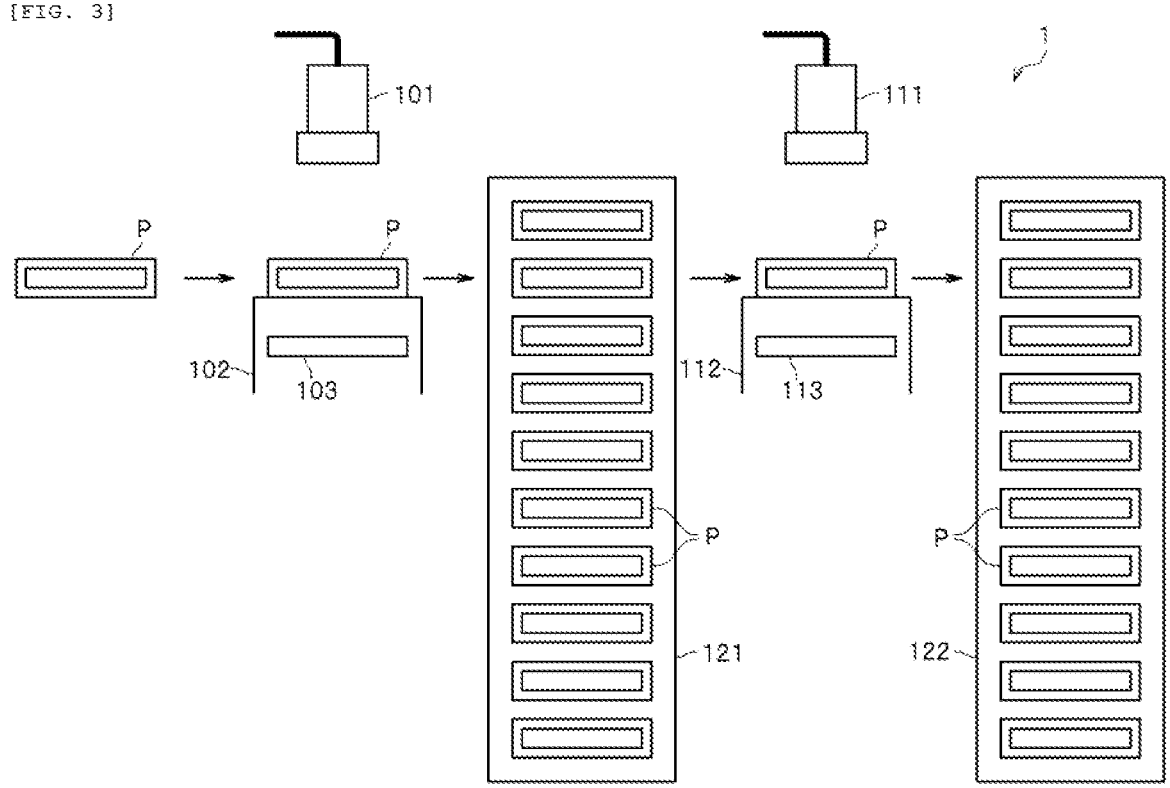
[FIG. 3]

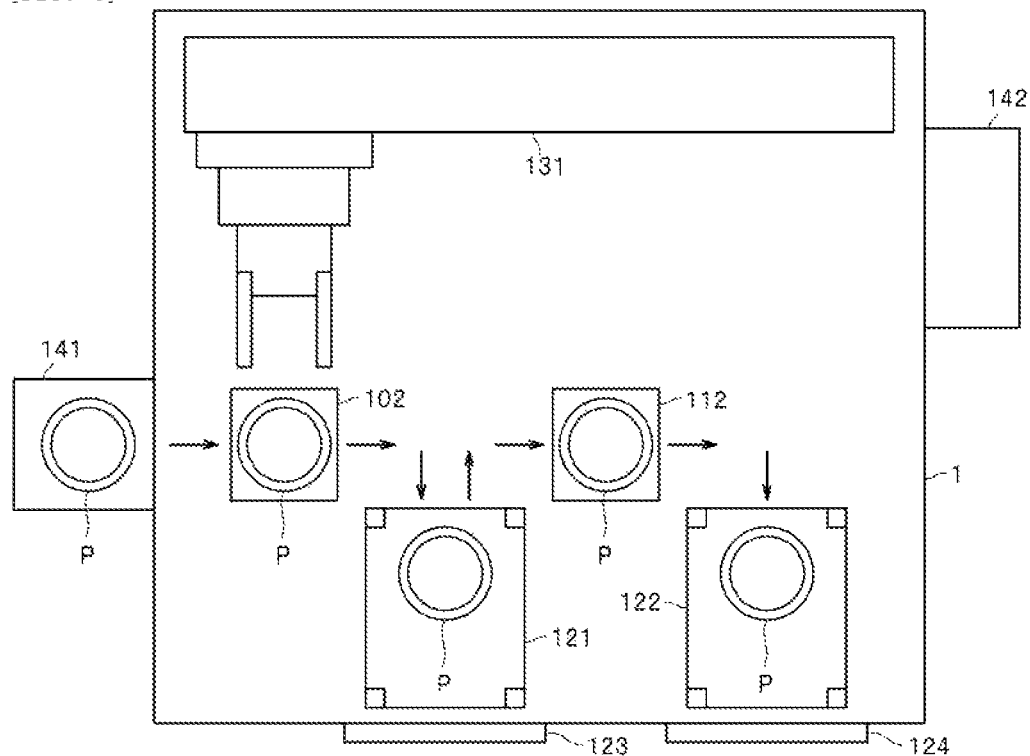

[FIG. 5]
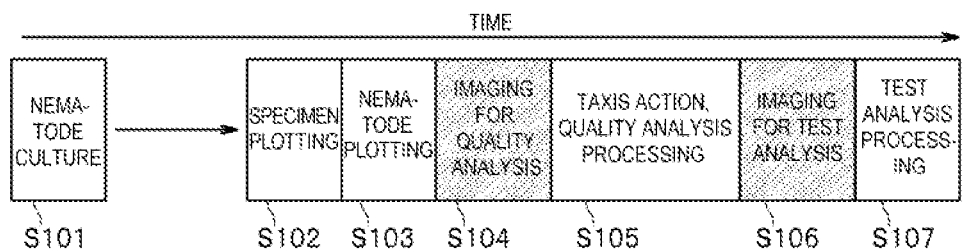

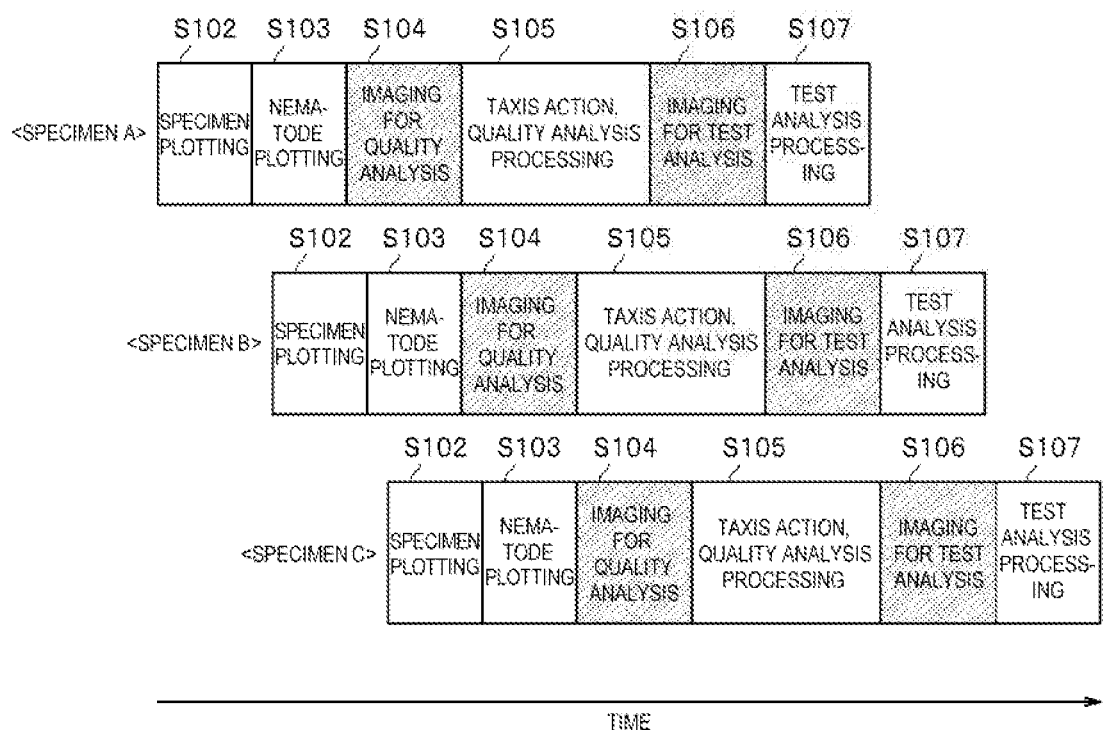
[FIG. 6]

[FIG. 7]
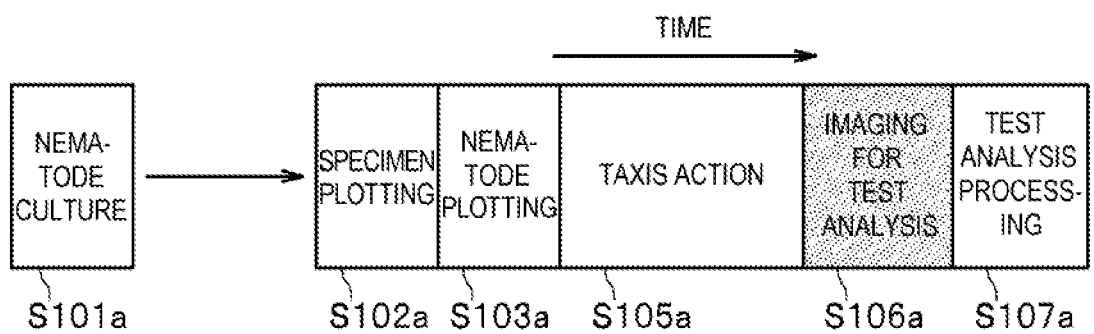

[FIG. 8]
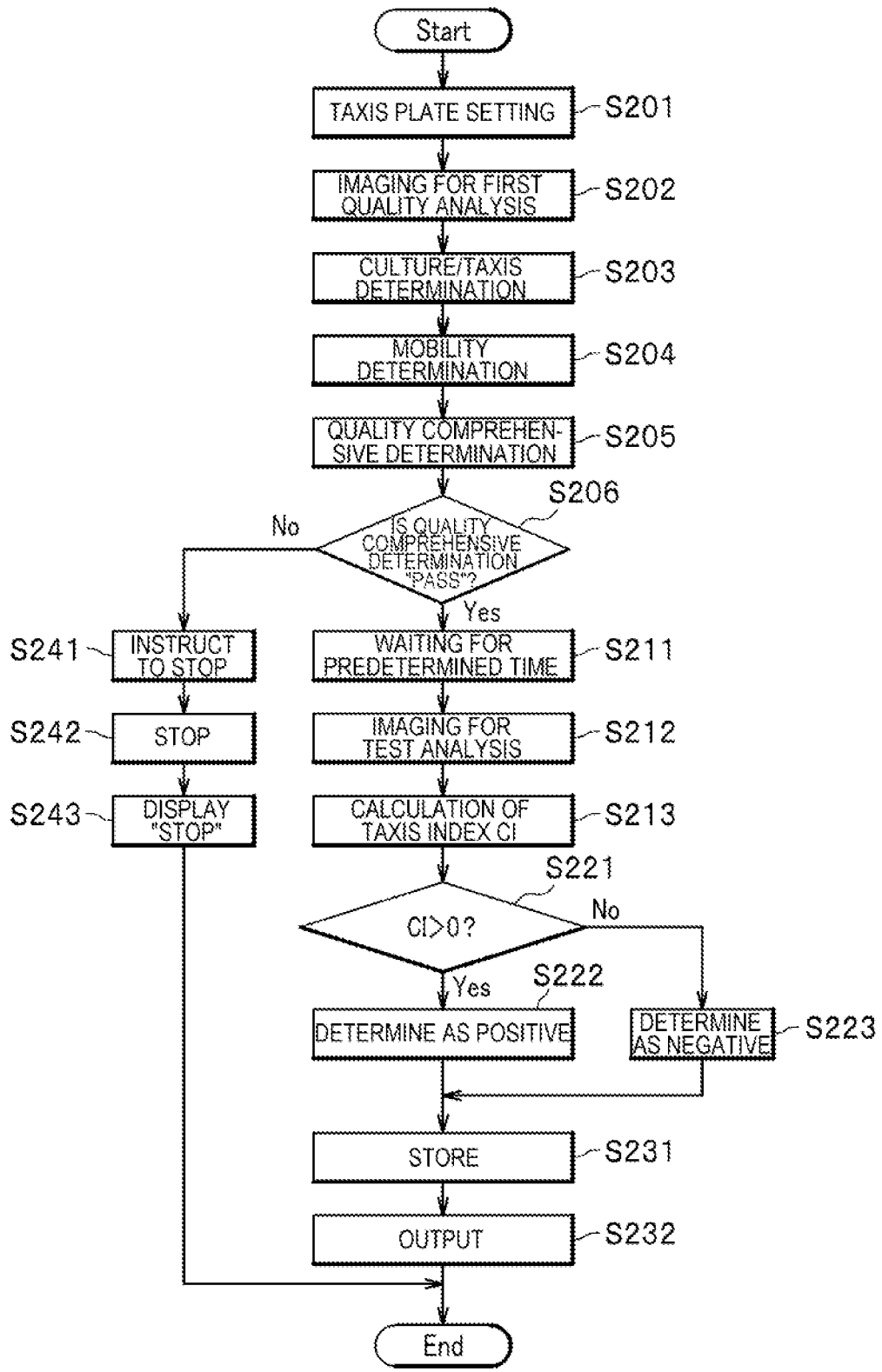

[FIG. 9]
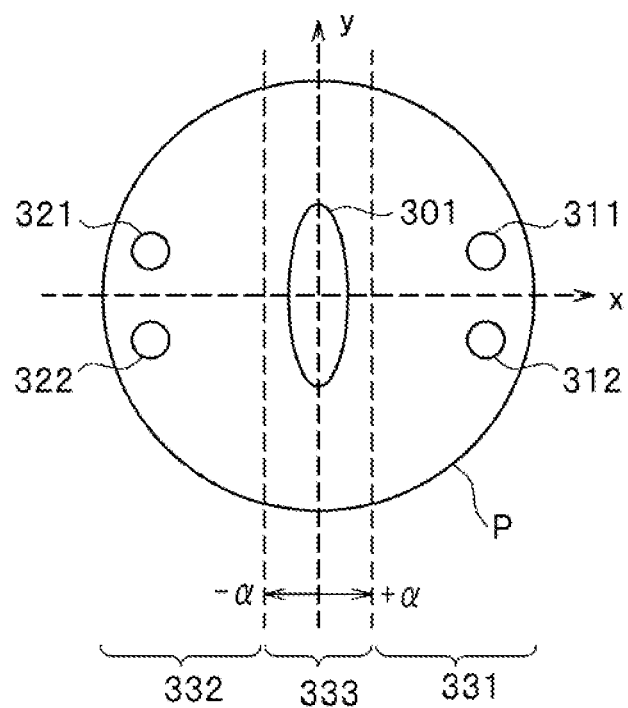

[FIG. 10]

| SPECI-MEN ID | CULTURE CONDITION ||| TAXIS CONDITION |||| CULTURE /TAXIS CONDI- TION DETERMI- NATION RESULT | MOBILITY M (mm) | MOBILITY DETERMI- NATION RESULT (M>8mm) | QUALITY COMPRE- HENSIVE RESULT | TAXIS INDEX CI | CANCER TEST RESULT |
|---|---|---|---|---|---|---|---|---|---|---|---|---|---|
| | ENVIRON- MENTAL TEMPERA- TURE (°C) | INOCULUM/ E. COLI 50μL | MEDIUM COMPO- SITION | ENVIRON- MENTAL TEMPERA- TURE (°C) | MEDIUM COMPO- SITION | TAXIS TIME (minutes) | NUMBER OF NEM- ATODES | | | | | | |
| P1 | 20±0.5 | 0.6 | B1 | 23±0.5 | B2 | 30 | 50 | PASS | 12 | PASS | PASS | 0.8 | P |
| P2 | 20±0.5 | 0.6 | B1 | 23±0.5 | B2 | 30 | 52 | PASS | 10 | PASS | PASS | 0.7 | P |
| P3 | 20±0.5 | 0.6 | B1 | 23±0.5 | B2 | 30 | 49 | PASS | 9 | PASS | PASS | 0.65 | P |
| P4 | 20±0.5 | 0.6 | B1 | 23±0.5 | B2 | 30 | 57 | PASS | 10 | PASS | PASS | −0.7 | N |
| P5 | 20±0.5 | 0.6 | B1 | 23±0.5 | B2 | 30 | 53 | PASS | 5 | FAIL | FAIL | 0.01 | FAIL |
| ... | ... | ... | ... | ... | ... | ... | ... | ... | ... | ... | ... | ... | ... |

231

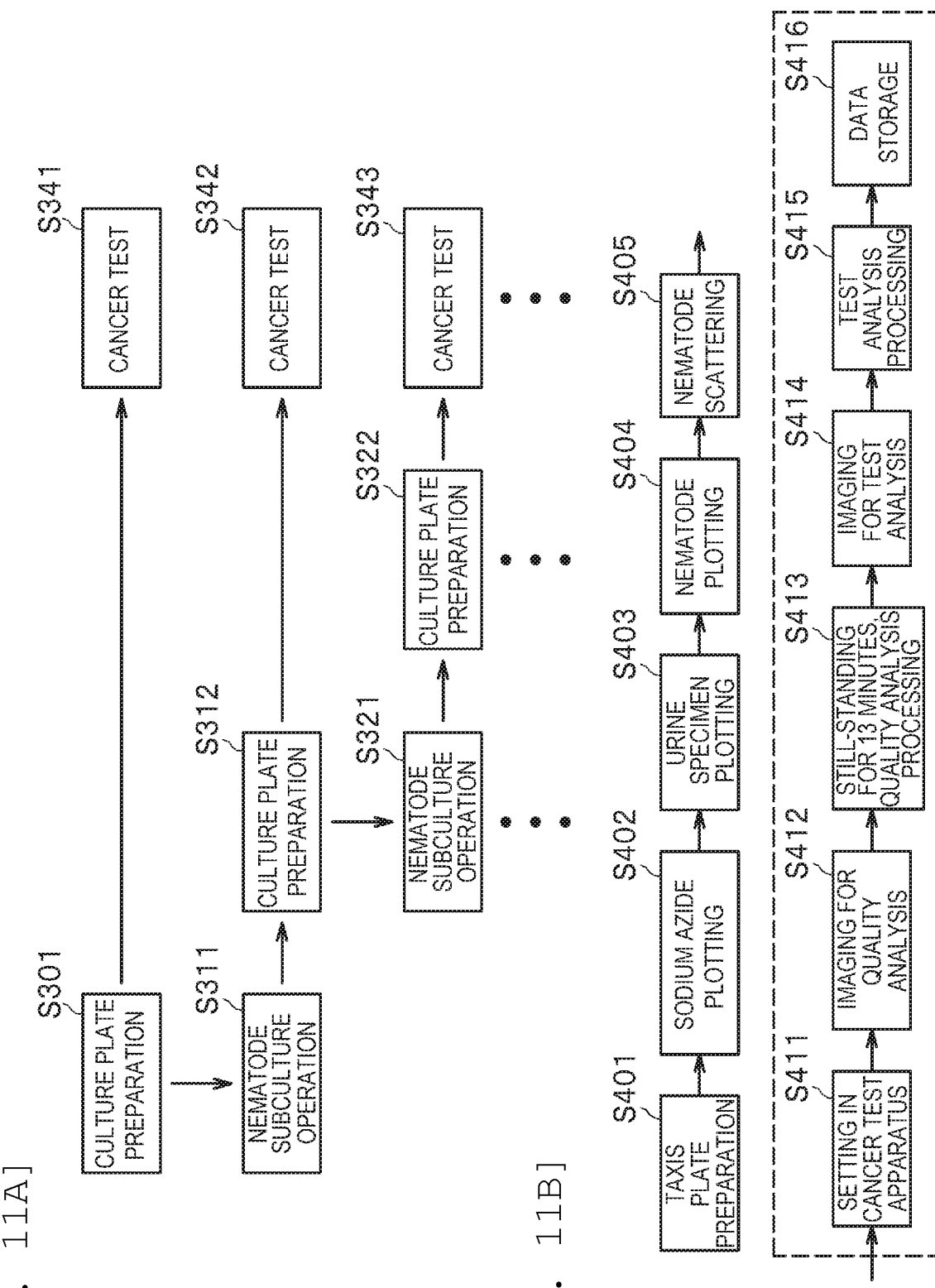

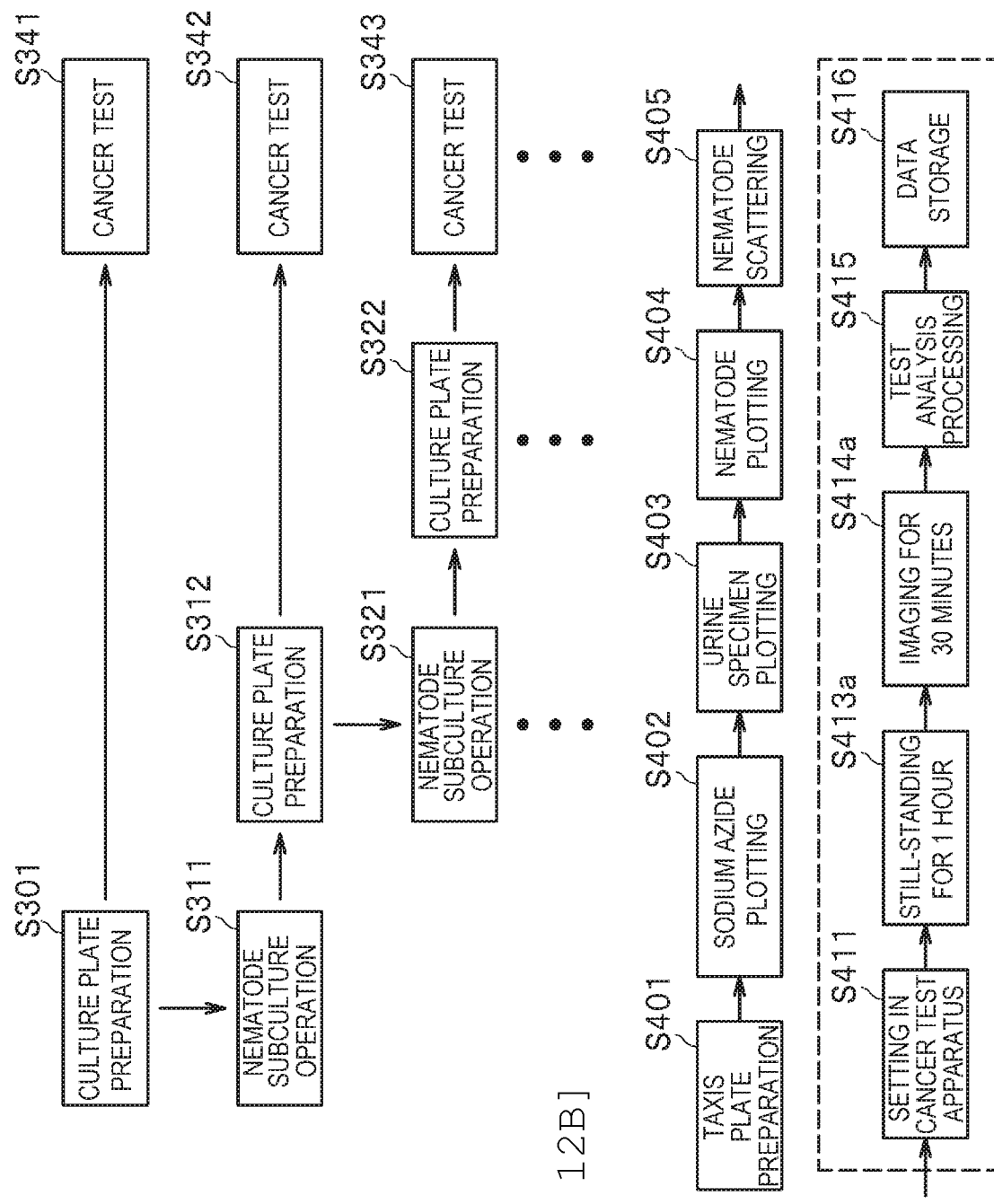

[FIG. 13A]
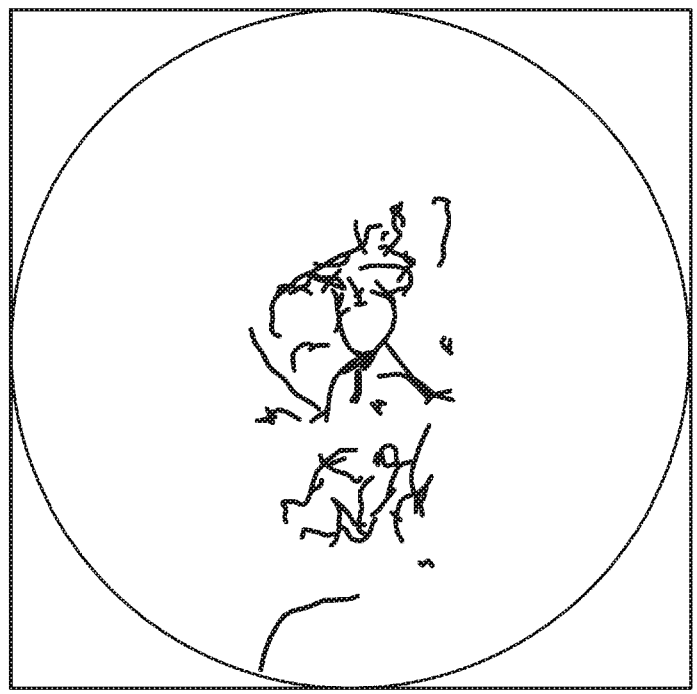
[FIG. 13B]
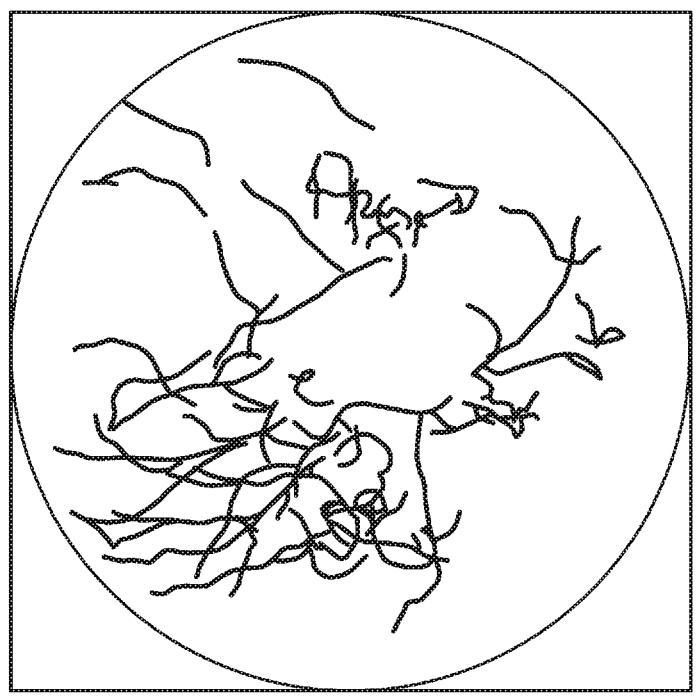

[FIG. 14]
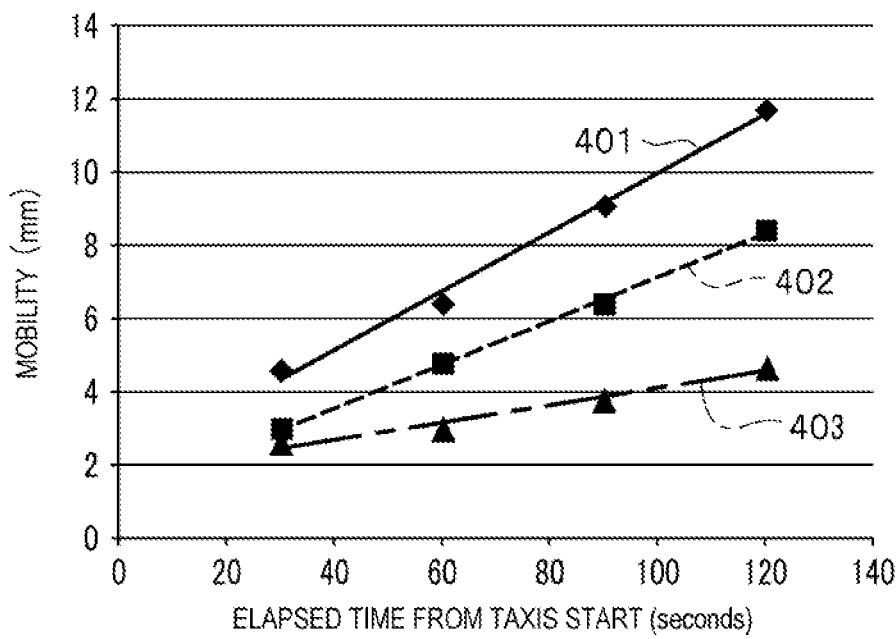
[FIG. 15]
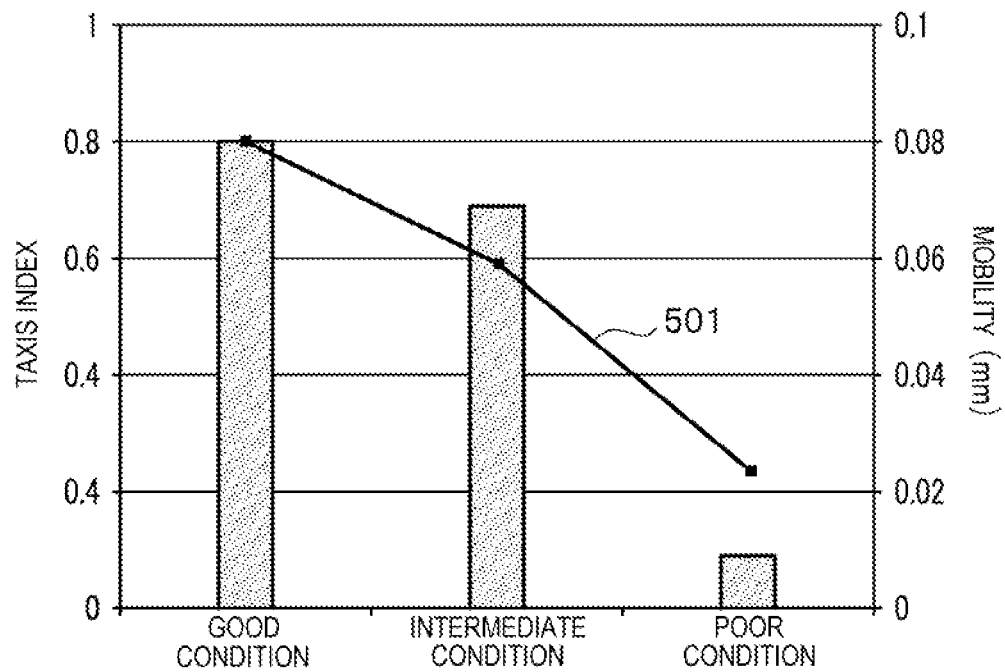

[FIG. 16]
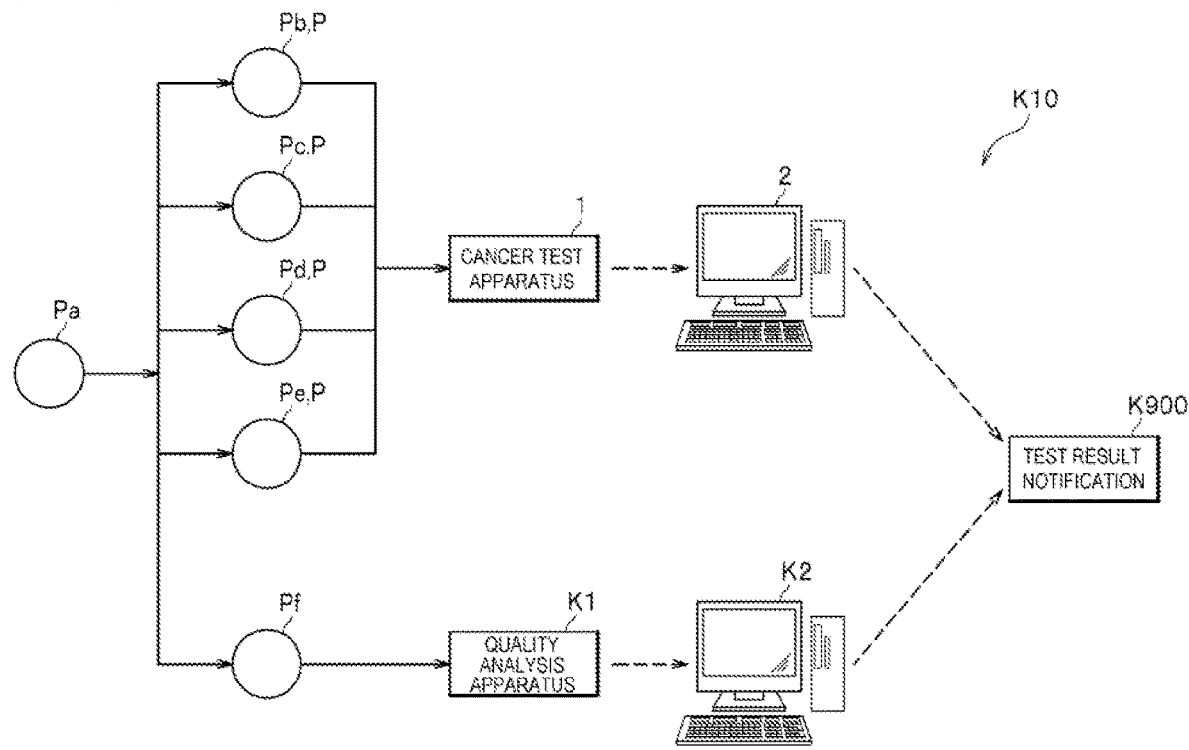

[FIG. 17]
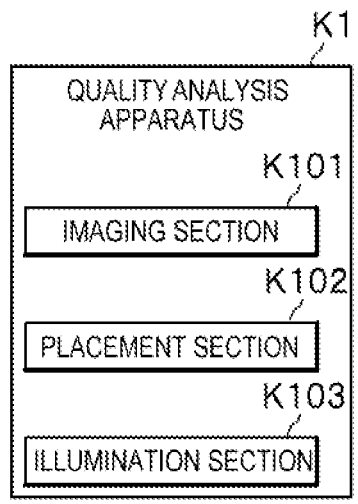
[FIG. 18]
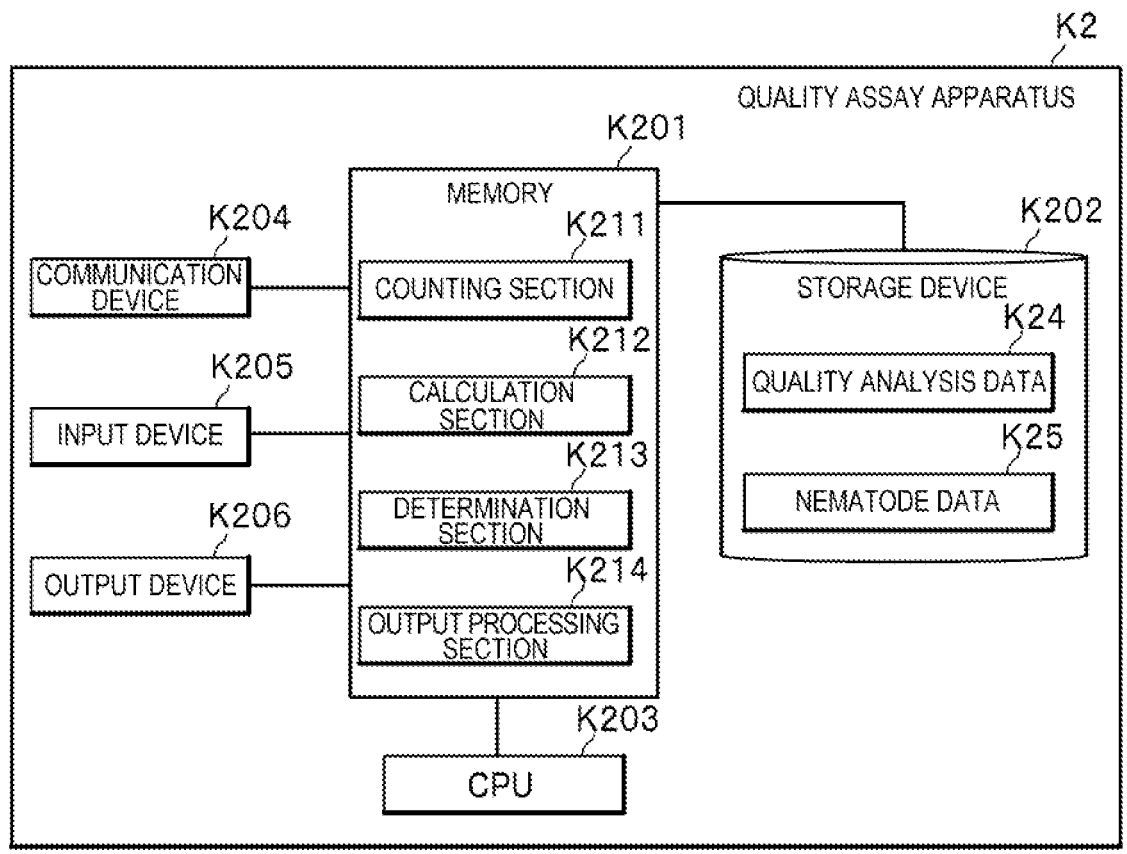

[FIG. 19]
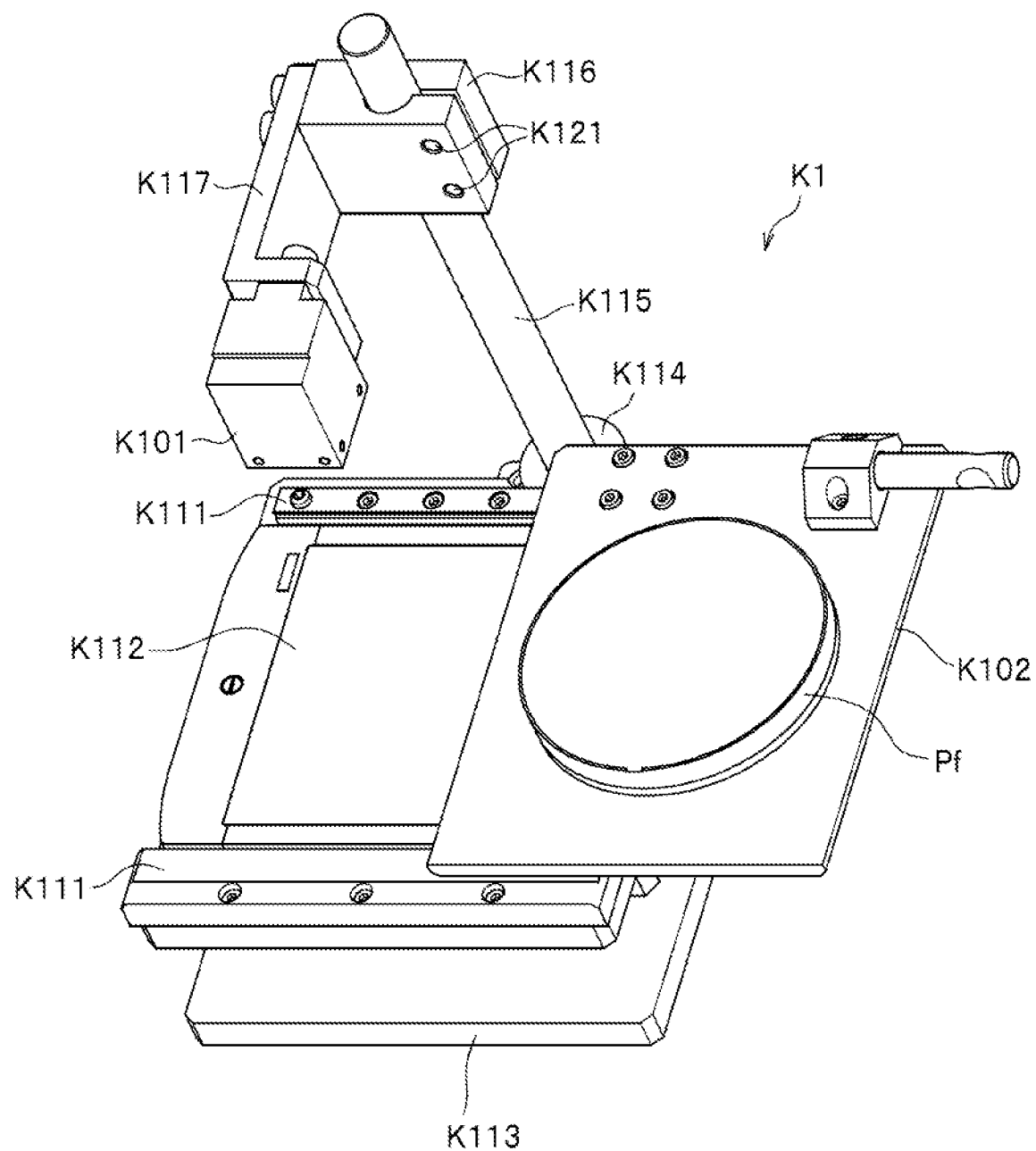

[FIG. 20]
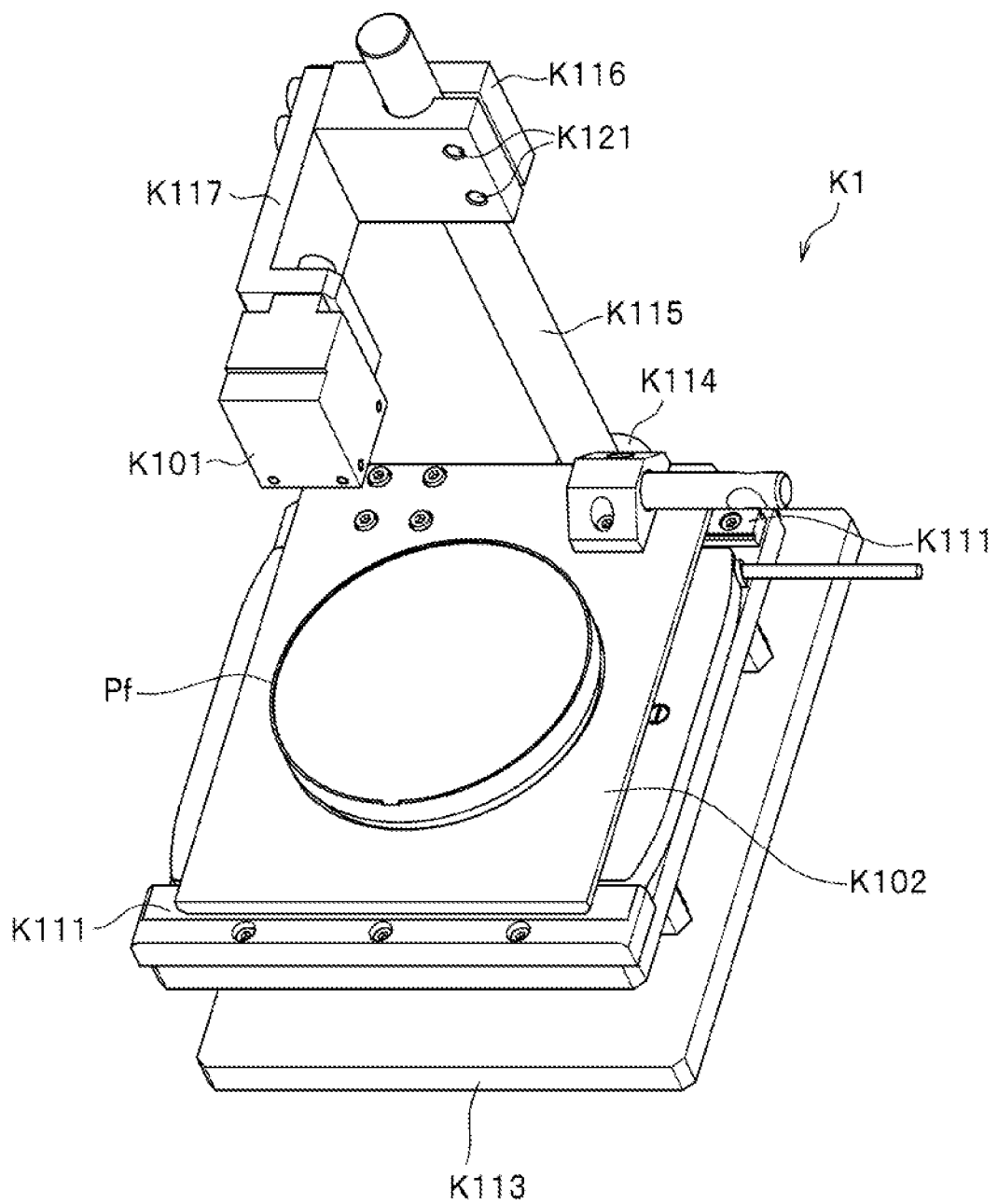

| PLATE ID | TAXIS TEMPERATURE (°C) | TAXIS TIME (minutes) | ILLUMINATION CONDITION | NEMATODE GROUP ID | NEMATODE TOTAL NUMBER | POSITIVE TAXIS | NEGATIVE TAXIS | NEUTRAL | TAXIS INDEX CI | STANDARD SUBSTANCE | ACCEPTABLE LINE |
|---|---|---|---|---|---|---|---|---|---|---|---|
| Pf1 | 23±0.5 | 30 | 30 | 4-1 | 52 | 41 | 4 | 7 | +0.82 | ISOAMYL ALCOHOL | CI>+0.7 |
| Pf2 | 23±0.5 | 30 | 30 | 4-2 | 55 | 46 | 3 | 6 | +0.87 | ISOAMYL ALCOHOL | CI>+0.7 |
| Pf3 | 23±0.5 | 30 | 30 | 4-3 | 48 | 23 | 20 | 5 | +0.07 | ISOAMYL ALCOHOL | CI>+0.7 |
| ... | ... | ... | ... | ... | ... | ... | ... | ... | ... | ... | ... |

| NEMATODE GROUP ID | INDIVIDUAL ID | TIME (SECONDS AFTER) | FERET DIAMETER (mm) | COORDI-NATE | MOVING DISTANCE (mm) | VELOCITY (mm/s) | AVERAGE FERET DIAMETER (mm) | AVERAGE MOVING DISTANCE (mm) | AVERAGE VELOCITY (mm/s) |
|---|---|---|---|---|---|---|---|---|---|
| 4-1 | 4-1-1 | 1 | 1 | 1,1 | 1 | 1 | 1.1 | 40 | 1.2 |
| | | 2 | 1.1 | 2,2 | 2 | 1.5 | | | |
| | | ... | ... | ... | ... | ... | | | |
| | | 3600 | 1.2 | 40,50 | 50 | 0 | | | |
| | 4-1-2 | 1 | 1 | 1,1 | 1 | 1 | | | |
| | | 2 | 1.1 | 2,2 | 2 | 1.5 | | | |
| | | ... | ... | ... | ... | ... | | | |
| | | 3600 | 1.2 | 40,50 | 50 | 0 | | | |
| | 4-1-3 | ... | ... | ... | ... | ... | | | |
| | 4-1-4 | ... | ... | ... | ... | ... | | | |
| | 4-1-5 | ... | ... | ... | ... | ... | | | |
| | ... | ... | ... | ... | ... | ... | | | |
| | 4-1-50 | ... | ... | ... | ... | ... | | | |
| ... | ... | ... | ... | ... | ... | ... | ... | ... | ... |
| ... | ... | ... | ... | ... | ... | ... | ... | ... | ... |

[FIG. 23]
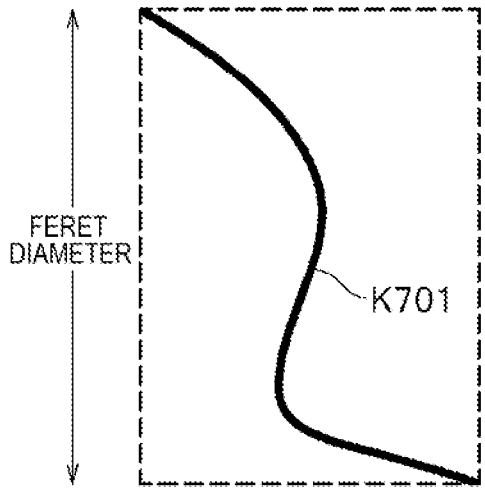
[FIG. 24]
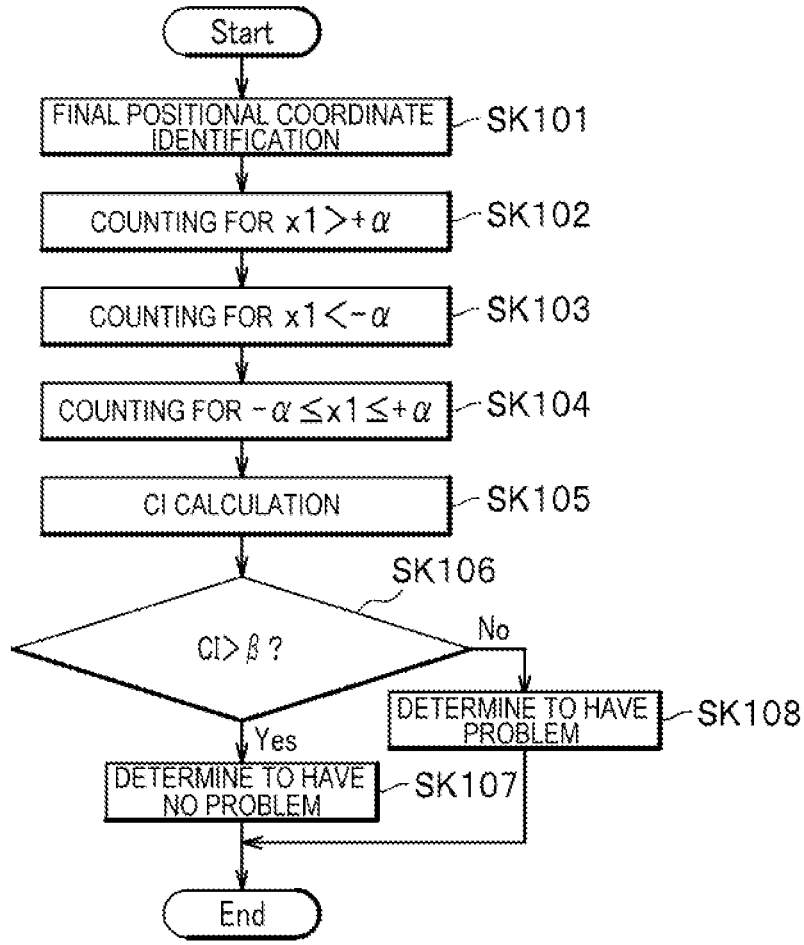

[FIG. 25]
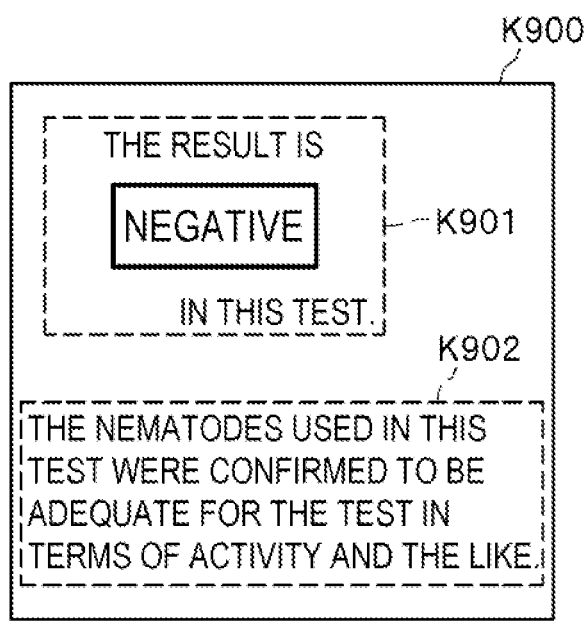

CANCER TEST SYSTEM AND METHOD FOR ASSESSING CANCER TEST

TECHNICAL FIELD

The present invention relates to a technique of a cancer test system for performing a cancer test using nematodes and of a method for assessing a cancer test.

BACKGROUND ART

A cancer test has been developed to use the fact that a nematode undergoes an attraction action to urine of a cancer patient and repelling actions to urine of a healthy subject.

PTL 1 discloses a method for detecting a cancer using the olfaction of a nematode.

CITATION LIST

Patent Literature

PTL 1: WO2015/088039

SUMMARY OF INVENTION

Technical Problem

In a cancer test using nematodes, how to achieve the quality control is one major problem. Here, the quality means whether or not the nematodes are adequate to the cancer test.

A nematode shows positive chemotaxis to urine of a cancer patient and negative chemotaxis to urine of a healthy subject as a result of optimization of various parameters. However, even if various parameters of the nematode culture condition (environmental temperature, inoculum on the culture medium (feed), medium composition, etc.) and the nematode chemotaxis condition (environmental temperature, medium composition, taxis time, etc.) are accurately controlled, this does not ensure good quality control. Chemotaxis will be hereinafter simply referred to as taxis.

Currently, a cancer test by nematodes is conducted manually by the following procedure.

(A1) A plate preparer prepares a plate for taxis on which nematodes undergo taxis (taxis plate). Specifically, the plate preparer subjects a mixture of agar and water to an autoclave. Then, after adding a reagent, such as potassium phosphate, potassium chloride, magnesium sulfate, or the like, the plate preparer dispenses the resultant mixture into the plate (petri dish) and cools the plate, thereby preparing a taxis plate having an agar medium.

(A2) A tester marks a point where nematodes are to be placed, a point where urine and sodium azide are to be plotted (dropwise added), and a point where sodium azide is to be plotted, on the agar medium on the prepared taxis plate. The marking is performed by putting marks on the plate (petri dish) with a felt-tip pen or the like. Incidentally, sodium azide is for paralyzing the nematodes.

Hereinafter, a mixture of urine and sodium azide will be referred to as urine+sodium azide.

(A3) The tester plots sodium azide with a pipette or the like on the marks made on the point where the urine+sodium azide is to be plotted and the point where sodium azide is to be plotted.

(A4) Next, the tester washes out nematodes cultured on a culture plate (petri dish) with buffer. Specifically, when the tester pours buffer throughout the culture plate, the nematodes float in the buffer, and thus, the tester sucks the floating nematodes with a pipette or the like, and then pours the sucked nematodes in a microtube or the like. Incidentally, the population of the nematodes on one culture plate is substantially constant.

(A5) Then, the tester washes the nematodes poured into the microtube with buffer. Specifically, the tester adds buffer into the microtube containing the poured nematodes in (A4). Then, the nematodes settle on the bottom of the microtube in 30 seconds, and then, the tester removes the supernatant (E. coli as feed), and adds buffer to the microtube again. The tester performs this operation three times to thereby wash the nematodes.

(A6) Subsequently, the tester plots urine on the taxis plate by plotting urine on the point where the urine+sodium azide is to be plotted marked in (A2).

(A7) Then, the tester plots the nematodes from the microtube of (A5) on the point where the nematodes are to be placed marked in (A2). The number of the nematodes to be plotted is desirably approximately 50. The number of the nematodes can be controlled by determining a condition, such as the amount of the buffer.

(A8) The tester spreads and slightly diffuses the plotted nematodes, and applies Kimwipe® or the like at the point where the nematodes are plotted to remove the excess buffer.

(A9) The nematodes are allowed to undergo taxis actions over about one hour.

(A10) After completion of the taxis, the tester counts the number of nematodes demonstrating attraction actions to urine and the number of nematodes demonstrating repelling actions thereto, calculates a taxis index (Chemotaxis Index; CI), and determines the positivity or negativity to a cancer based on the calculated taxis index.

Here, the inventors have found that differences arise in the test result depending on the individual skill of the tester. For example, when the nematodes come in contact with the pipette, Kimwipe®, or the like in the operation in (A4), (A5), (A7), or (A8) mentioned above, the nematodes weaken due to damages thereof or other reasons and a good test result can not be obtained. Alternatively, in the operation of (A8), when the tester can not completely remove the buffer, the nematodes can not move out of the buffer and a good test result can not be obtained.

For such reasons, a nematode quality assurance that secures that the quality of nematodes used in the cancer test is adequate is essential for enhancing the reliability in results of the cancer test.

The present invention has been made against the above background, and an object of the invention is to efficiently perform quality determination of nematodes used in a cancer test using the nematodes.

Solution to Problem

For solving the above problem, a cancer test system of the present invention is characterized by comprising: a quality information acquisition section that acquires, in response to placement of a plate on which a urine from a subject and a nematode are set, information on taxis action for quality assay of the nematode during the initial predetermined time; a first taxis information generation section that generates first taxis information which is first information on taxis action of the nematode based on the information acquired by the quality information acquisition section; a quality determination section that determines a quality of the nematode based on the first taxis information; a test information acquisition section that acquires information on taxis action for cancer test assay by the nematode; a second taxis information generation section that generates second taxis information which is second information on taxis action of the nematode based on the information acquired by the test information acquisition section; and a cancer test determination section that determines the presence or absence of a cancer in the subject, which is a source of the urine, based on the second taxis information.

Other means for resolution will be described later in the embodiments.

Advantageous Effects of Invention

According to the present invention, quality determination of the nematodes used in a cancer test using nematodes can be efficiently performed.

BRIEF DESCRIPTION OF DRAWINGS

FIG. 1 shows a configuration example of a cancer test system according to a first embodiment.

FIG. 2 is a functional block diagram showing a configuration example of an analysis apparatus according to the first embodiment.

FIG. 3 is a schematic side view of a cancer test apparatus according to the first embodiment.

FIG. 4 is a schematic top view of the cancer test apparatus according to the first embodiment.

FIG. 5 shows a schematic procedure of a cancer test using nematodes according to the first embodiment.

FIG. 6 shows a continuous assay of a first quality assay according to the first embodiment.

FIG. 7 shows a procedure of a conventional cancer test using nematodes (Comparative Example).

FIG. 8 is a flowchart showing a detailed procedure of a first quality assay processing according to the first embodiment.

FIG. 9 shows a plotting example of a specimen and the nematodes according to the first embodiment.

FIG. 10 shows an example of cancer test data according to the first embodiment.

FIGS. 11A and 11B show examples of the detailed procedure for the cancer test according to the first embodiment. FIG. 11A shows a culture process and FIG. 11B shows a cancer test process.

FIGS. 12A and 12B show examples of processes of a cancer test in Comparative Example. FIG. 12A shows a culture process and FIG. 12B shows a cancer test process.

FIGS. 13A and 13B show examples of an image for the first quality assay of nematodes according to the first embodiment. FIG. 13A shows an example in which the movement of nematodes is not good and FIG. 13B shows an example in which the movement of nematodes is good.

FIG. 14 shows a relationship between the plotting condition and the mobility according to the first embodiment.

FIG. 15 shows the mobility and a relationship to the taxis index according to the first embodiment.

FIG. 16 shows a configuration example of a cancer test system according to a second embodiment.

FIG. 17 is a functional block diagram showing a configuration example of a quality assay apparatus according to the second embodiment.

FIG. 18 is a functional block diagram showing a configuration example of a quality analysis apparatus according to the second embodiment.

FIG. 19 shows an example of a specific configuration of the quality assay apparatus according to the second embodiment (No. 1).

FIG. 20 shows the example of a specific configuration of the quality assay apparatus according to the second embodiment (No. 2).

FIG. 21 shows a configuration example of quality assay data according to the second embodiment.

FIG. 22 shows a configuration example of nematode data according to the second embodiment.

FIG. 23 shows a Feret diameter.

FIG. 24 is a flowchart showing a procedure of a test assay processing according to the second embodiment.

FIG. 25 shows an example of a test result notification according to the second embodiment.

DESCRIPTION OF EMBODIMENTS

Next, modes for implementing the present invention (referred to as "embodiments") will be described in detail with reference to drawings as needed. Incidentally, in the drawings, the same signs are used for the respective same components to omit the explanation.

Hereinunder, a taxis assay for testing the positivity or negativity in terms of a cancer in a subject using urine from the subject is referred to as a test assay, and a taxis assay for determining whether or not nematodes used in the cancer test is adequate for the test is referred to as a quality assay.

First Embodiment

In a first embodiment, taxis actions of nematodes are observed during the initial few minutes (2 minutes here) from the start of a taxis assay for a cancer test, and from the observation result, a quality assay of the nematodes is performed. Incidentally, the quality assay in the first embodiment is referred to as a first quality assay to distinguish it from a quality assay in a second embodiment.

System Configuration

FIG. 1 shows a configuration example of a cancer test system according to the first embodiment.

A cancer test system 10 includes a cancer test apparatus 1, a control apparatus 3, an analysis apparatus 2, and a display apparatus 4.

The cancer test apparatus 1 images actions of the nematodes for the cancer test, and also images actions of the nematodes for the first quality assay for determining whether or not the nematodes used in the cancer test are adequate for the cancer test.

The control apparatus 3 controls sections of the cancer test apparatus 1 and sends images captured in the cancer test system 10 to the analysis apparatus 2. The control apparatus 3 is a personal computer (PC) or the like.

The analysis apparatus 2 assays the taxis actions of the nematodes based on the images received from the control apparatus 3, thereby performing the first quality assay and also performing an assay of the cancer test (test assay). In addition, the analysis apparatus 2 sends the result of the first quality assay to the control apparatus 3, as required.

The display apparatus 4 is connected to the control apparatus 3, and shows the steps for each taxis plate P, and displays the result of the first quality assay that the control apparatus 3 receives from the analysis apparatus 2.

Analysis Apparatus

FIG. 2 is a functional block diagram showing a configuration example of the analysis apparatus according to the first embodiment.

The analysis apparatus 2 is, for example, a PC or the like, and includes a memory 201, a central processing unit (CPU) 202, a storage device 203, a communication device 204, an input device 205, and an output device 206.

The communication device 204 sends data to and receives data from the control apparatus 3 and the like.

The input device 205 is a keyboard, a mouse, or the like.

The output device 206 is a printer or the like in this embodiment and prints a test result notification.

The storage device 203 is a hard disk (HD), a solid state drive (SSD), or the like which stores cancer test data 231 and the like described later.

In the memory 201, a program stored in the storage device 203 is loaded. The loaded program is executed by the CPU 202 to thereby embody an image processing section 211, a mobility calculation section (first taxis information generation section) 212, a taxis index calculation section (second taxis information generation section) 213, a quality determination processing section (quality determination section) 214, a test determination processing section (cancer test determination section) 215, and an output processing section 216.

The image processing section 211 processes an image sent from the control apparatus 3 (FIG. 1) to facilitate the first quality assay and the test assay on the image.

The mobility calculation section 212 calculates a mobility which is an average moving distance of the nematodes (information on the distance the nematodes have moved) from the image captured for the first quality assay and subjected to image processing by the image processing section 211 (image for first quality assay; information on taxis action for quality assay). The mobility will be described later.

The taxis index calculation section 213 calculates a taxis index of the nematodes from the image captured for the test assay and subjected to image processing by the image processing section 211 (image for test assay; information on taxis action for test assay). The taxis index will be described later.

The quality determination processing section 214 determines whether or not the nematodes used in the cancer test are adequate for the cancer test based on the mobility calculated by the mobility calculation section 212.

The test determination processing section 215 performs the determination on the cancer test based on the taxis index calculated by the taxis index calculation section 213.

The output processing section 216 allows the output device 206 to output the determination result given by the quality determination processing section 214 and the determination result given by the test determination processing section 215.

Cancer Test Apparatus

FIG. 3 is a schematic side view of the cancer test apparatus according to the first embodiment, and FIG. 4 is a schematic top view of the cancer test apparatus according to the first embodiment.

As shown in FIG. 3 and FIG. 4, the cancer test apparatus 1 includes a camera for quality assay (quality information acquisition section, imaging section) 101, an imaging stage for quality assay (imaging stage) 102, a light source for quality assay 103, a camera for test assay (test information acquisition section) 111, an imaging stage for test assay 112, a light source for test assay 113, a storage chamber 121, a discard chamber 122, a movement device 131, a plate placement stage 141, and a temperature control device 142.

Incidentally, for the sake of avoiding complexity, the movement device 131, the plate placement stage 141, and the temperature control device 142 are omitted in FIG. 3, and the camera for quality assay 101, the camera for test assay 111, the light source for quality assay 103, and the light source for test assay 113 are omitted in FIG. 4.

The camera for quality assay 101 is a camera that performs an imaging for first quality assay which is an imaging for performing the first quality assay.

The imaging stage for quality assay 102 is a stage on which a taxis plate P is placed when the imaging by the camera for quality assay 101 is performed.

The light source for quality assay 103 is a light source for illuminating the taxis plate P from below during the imaging for first quality assay is performed. Thus, the imaging stage for quality assay 102 is composed of a light-transmissive member.

The camera for test assay 111 is a camera that performs an imaging for test assay which is an imaging for performing the test assay of the nematodes.

The imaging stage for test assay 112 is a stage on which the taxis plate P is placed when the imaging by the camera for quality assay 101 is performed.

The light source for test assay 113 is a light source for illuminating the taxis plate P from below during the imaging for test assay is performed. Thus, the imaging stage for test assay 112 is composed of a light-transmissive member.

The storage chamber 121 is a place for allowing the taxis plate P to stand still to allow the nematodes to undergo taxis actions after completion of the imaging for first quality assay. Incidentally, it is desired that the storage chamber 121 is shielded against light to allow the taxis plate P to stand still in a dark space. As shown in FIG. 4, the storage chamber 121 may be provided with a storage chamber outlet port 123 from which the taxis plate P rejected as a result of the first quality assay is taken out.

The discard chamber 122 is a place where the taxis plate P that is to be discarded is placed after completion of the imaging for test assay. After the completion of the imaging for test assay, the taxis plate P is transported to the discard chamber 122 and taken out through a discard chamber outlet port 124.

The camera for quality assay 101 and the camera for test assay 111 may be the same camera. The imaging stage for quality assay 102 and the imaging stage for test assay 112 may be the same stage. The light source for quality assay 103 and the light source for test assay 113 may also be the same light source.

In addition, the light source for quality assay 103 and the light source for test assay 113 are desirably a light emitting diode (LED) or LEDs, but may not be limited to LED(s).

The movement device 131 is a manipulator or the like which is movable in the x-axis direction and the y-axis direction by a dual-axis slider or the like and performs a movement of the taxis plate P.

The plate placement stage 141 is a place on which the taxis plate P is first placed.

The temperature control device 142 is a device that controls the temperatures of the imaging stage for quality assay 102, the imaging stage for test assay 112, the storage chamber 121, and the like to an optimal temperature for the nematodes.

Once the cancer test is started, first, the taxis plate P is placed on the plate placement stage 141, whereby the taxis plate P is set in the cancer test apparatus 1.

After that, the movement device 131 places the taxis plate P on the imaging stage for quality assay 102. For example, a weight detection device (not shown) is provided to the imaging stage for quality assay 102, and the weight detection device detects the placement of the taxis plate P on the imaging stage for quality assay 102 by detecting the weight change. Upon detecting the placement of the taxis plate P on the imaging stage for quality assay 102, the control apparatus 3 allows the camera for quality assay 101 to image the taxis plate P for 2 minutes to thereby perform the imaging for first quality assay. In this way, the timing of the start of the imaging for first quality assay can be equalized for all the plates P.

Incidentally, upon detecting the placement of the taxis plate P on the imaging stage for quality assay 102, the control apparatus 3 turns on the light source for quality assay 103.

After the imaging for first quality assay is completed, the movement device 131 stores the taxis plate Pin the storage chamber 121. The taxis plate P is allowed to stand still in the storage chamber 121, for example, for 13 minutes, whereby the nematodes undergo taxis actions. At this time, information about the taxis plate P rejected as a result of the first quality assay is displayed on the display apparatus 4 (see FIG. 1), and the tester may take out the corresponding taxis plate P through the storage chamber outlet port 123 based on the information displayed on the display apparatus 4.

The taxis plate P allowed to stand still for 13 minutes in the storage chamber 121 is placed on the imaging stage for test assay 112 by the movement device 131. For example, a weight detection device (not shown) is provided to the imaging stage for test assay 112, and the weight detection device detects the placement of the taxis plate P on the imaging stage for test assay 112 by detecting the weight change. Upon detecting the placement of the taxis plate P on the imaging stage for test assay 112, the control apparatus 3 allows the camera for test assay 111 to image the taxis plate P for 5 seconds to thereby perform the imaging for test assay. Incidentally, upon detecting the placement of the taxis plate P on the imaging stage for test assay 112, the control apparatus 3 turns on the light source for test assay 113.

After the imaging for test assay is completed, the movement device 131 stores the taxis plate P in the discard chamber 122. The taxis plate P stored in the discard chamber 122 is discarded.

Summary of Cancer Test Procedure

FIG. 5 shows a schematic procedure of the cancer test using nematodes according to the first embodiment. In FIG. 5 to FIG. 7, FIG. 1 to FIG. 4 are referred to as needed.

As shown in FIG. 5, in this embodiment, after culturing the nematodes (S101), the tester plots (sets) a specimen in the prepared taxis plate P (S102). Here, the specimen is a urine from a subject. Subsequently, the tester plots the nematodes on the taxis plate P (S103), and when the taxis plate P is then set in the cancer test apparatus 1 and taxis actions of the nematodes are started, the imaging for quality assay by the camera for quality assay 101 is performed during the initial 2 minutes (S104). The imaging for quality assay here is the imaging for first quality assay.

Then, the taxis plate P is moved into the storage chamber 121, and the nematodes are allowed to undergo taxis actions while a quality assay processing is performed using the image for first quality assay captured in Step S103 (S105). As used herein, the quality assay processing is a first quality assay processing. The first quality assay processing will be described in detail later.

After a sufficient time period for the taxis actions of the nematodes elapses (approximately 13 minutes), the imaging for test assay is performed by the camera for test assay 111 (S106).

Then, using the image for test assay captured in Step S106, a test assay processing is performed (S107).

In this way, since the quality assay can be performed while allowing the nematodes to undergo the taxis actions for the cancer test, the quality assay can be performed in an efficient manner.

In addition, the quality assay can be performed for all the taxis plates P to be subjected to the cancer test. In other words, a hundred-percent assay can be performed for the quality assay.

FIG. 6 shows a continuous assay of the first quality assay according to the first embodiment.

Here, for each of a specimen A, a specimen B, and a specimen C, a cancer test is performed by the same procedure as in FIG. 5. In FIG. 6, the treatments S102 to S107 for each specimen are the same as the treatments S102 to S107 in FIG. 5, and hence the explanation is omitted. Incidentally, as described above, each specimen is a urine from a subject, and the specimens correspond to the respective taxis plates P.

As shown in FIG. 6, the imaging for quality assay is performed for 30 seconds to 2 minutes from the start of the taxis actions of the nematodes, whereby the taxis plate P of the specimen A is moved into the storage chamber 121 upon completion of the imaging for first quality assay of the specimen A and immediately after that, the imaging for first quality assay for the specimen B is performed. Then, the taxis plate P of specimen B is moved into the storage chamber 121 upon completion of the imaging for first quality assay for the specimen B, and immediately after that, the imaging for first quality assay for the specimen C is performed. That is, the time for the imaging for quality assay is not limited to 30 seconds to 2 minutes as long as there is an enough time to achieve the still-standing in the storage chamber 121 in parallel for a plurality of plates P.

As described above, according to this embodiment, the imaging for first quality assay can be continuously performed to promote an efficient operation.

FIG. 7 shows a procedure for a conventional cancer test using nematodes (Comparative Example).

As shown in FIG. 7, in the conventional cancer test using nematodes, after culturing the nematodes (S101a), a specimen is plotted on a taxis plate P (S102a), the nematodes are plotted on the taxis plate P (S103a), and the nematodes are allowed to undergo taxis actions (S105a), followed by imaging for test assay (S106a). Then, on the basis of the captured image, the positions of the nematodes on the taxis plate P are determined and the number thereof is counted, and on the basis of the counting result, determination of the cancer test (test assay processing: S107a) is performed.

That is, a great difference between Comparative Example and the first embodiment is the presence or absence of Step S104.

Flowchart

FIG. 8 is a flowchart showing a detailed procedure of the first quality assay processing according to the first embodiment. FIG. 1 to FIG. 4 are referred to as needed.

First, the taxis plate P for performing a cancer test is set in the cancer test apparatus 1 (S201). Here, in the set taxis plate P, the urine+sodium azide, sodium azide, and the nematodes are plotted at predetermined positions.

Plotting Example

Here, a method for plotting a specimen and nematodes is explained with reference to FIG. 9.

FIG. 9 shows a plotting example of the specimen and the nematodes according to the first embodiment.

As shown in FIG. 9, sodium azide for paralyzing the nematodes is plotted at two points of an area 321 and an area 322. Then, the urine and sodium azide (urine+sodium azide) are plotted at two points of an area 311 and an area 312.

Here, the direction parallel to the line linking the area 321 and the area 311 is taken as the x-axis, and the direction perpendicular to the x direction is taken as the y-axis.

Then, as shown in FIG. 9, the nematodes are plotted at an area 301 at the center of the taxis plate P. As shown in FIG. 9, the area 301 where the nematodes are to be plotted has a width in the y-axis direction.

Incidentally, in the example of FIG. 9, each of the sodium azide and the urine+sodium azide is plotted at two points, but the number of the points is not limited to two.

Incidentally, "α" and the areas 331 to 333 in FIG. 9 will be described later.

The description is now returned to FIG. 8 again.

Next, once the taxis actions of the nematodes are started, the control apparatus 3 allows the camera for quality assay 101 to image the nematodes in the taxis plate P during the initial 2 minutes (the imaging for first quality assay) (S202). In the imaging, photographs may be taken in a time-lapse manner, a movie may be taken, or the trajectories of the nematodes may be taken by opening the shutter for 2 minutes. As described above, the imaging for first quality assay is started based on the change of the placed substance on the imaging stage for quality assay 102.

Next, the quality determination processing section 214 performs culture/taxis conditions determination (S203). In Step S203, the quality determination processing section 214 determines whether or not the culture condition of the nematodes and the taxis condition of the cancer test meet predetermined conditions. Detailed description of Step S203 will be made later.

Then, the image processing section 211 performs image-processing on the image for first quality assay captured in Step S202, and the quality determination processing section 214 performs mobility determination using the image for first quality assay after the image-processing (S204).

Specifically, the processing in Step S204 is performed according to the following procedure.

(B1) The image processing section 211 performs a processing, such as strengthening the contrast, on the captured image for first quality assay, thereby facilitating recognition of the nematodes.

(B2) Then, the mobility calculation section 212 calculates a mobility M.

(B3) The quality determination processing section 214 determines whether or not the mobility M calculated is equal to or more than a predetermined threshold. A value equal to or more than the threshold is accepted and a value less than the threshold is rejected.

Here, examples of the method for calculating the mobility M include the following methods (C1) to (C4). Hereinunder, as shown in FIG. 9, the nematodes are plotted in the area 301 at the center of the taxis plate P, sodium azide is plotted in the areas 321 and 322 on the left side of the paper, and the urine+sodium azide is plotted in the areas 311 and 312 on the right side of the paper. The x-axis and the y-axis are defined in the directions as shown in FIG. 9. When the nematodes undergo the attraction action to the urine from the subject, the nematodes move to the positive direction in the x-axis. In the following description, the "n" is a number indicating an individual nematode, and "N" shows the total number of the nematodes on the taxis plate P. In addition, in the following description, Xn is a position in the x-coordinate of the nematode of No. "n", and Yn is a position in the y-coordinate of the nematode of No. "n".

(C1) In the case where the imaging during the initial 2 minutes is a movie capturing or a time-lapse imaging: the mobility calculation section 212 calculates, as the moving distance of the nematodes in a fixed time, $\Sigma(Xn^2+Yn^2)^{1/2}$, which is the sum of the moving distances from the origin for every frame rate or for every image. Then, the mobility calculation section 212 calculates the mobility M by calculating $\Sigma_t(\Sigma(Xn^2+Yn^2)^{1/2})/N$, which is the time average of the sum of the moving distances of all the nematodes.

(C2) In the case where the imaging during the initial 2 minutes is a movie capturing or a time-lapse imaging: the mobility calculation section 212 calculates, as the moving distance of the nematodes in a fixed time, $\Sigma(Xn)$, which is the sum of the moving distances in the horizontal direction for every frame rate or for every image. Next, the mobility calculation section 212 calculates the mobility M by calculating $\Sigma_t (\Sigma(Xn))/N$, which is the time average of the sum of the moving distances of all the nematodes.

(C3) In the case where static images are captured by continuously imaging during the initial 2 minutes: the mobility calculation section 212 calculates the mobility M by calculating $(\Sigma(Xn^2+Yn^2)^{1/2})/N$, which is the average of the sum of the distances from the origin of all the nematodes after a fixed time.

(C4) In the case where static images are captured by continuously imaging during the initial 2 minutes: the mobility calculation section 212 calculates the mobility M by calculating $\Sigma(Xn)/N$, which is the average of the sum of the distances in the horizontal direction of all the nematodes after a fixed time.

By calculating the mobility M as described above and performing a quality assay based on the mobility M as described later, a quantitative quality assay can be performed.

Incidentally, when the method of (C4) is used, the processing load can be reduced.

The description is now returned to FIG. 8 again.

Subsequently, the quality determination processing section 214 performs a quality comprehensive determination (S206). In Step S206, the quality determination processing section 214 determines whether or not the culture condition of the nematodes and the taxis condition for the cancer test meet predetermined conditions in Step S203 and in addition, the mobility M is equal to or more than a predetermined threshold.

As a result of Step S206, when the culture condition of the nematodes and the taxis condition of the cancer test meet the predetermined conditions and the mobility M is equal to or more than the predetermined threshold (Step S206→Yes), the quality determination processing section 214 determines that the nematodes used meet the quality condition.

Then, after allowing the nematodes to undergo taxis actions by waiting for the predetermined time (for example, 13 minutes) (S211), the control apparatus 3 allows the camera for test assay 111 to perform imaging of the nematodes in the taxis plate P (imaging for test assay) (S212). The captured image (image for test assay) is sent from the control apparatus 3 to the analysis apparatus 2.

Next, the taxis index calculation section 213 calculates a taxis index CI using the image for test assay captured in Step S212 (S213).

The calculation of taxis index CI in Step S213 is performed as follows. FIG. 9 will be referred to as needed.

(D1) First, the taxis index calculation section 213 identifies positions (final positional coordinates) of the nematodes after migration.

(D2) Then, the taxis index calculation section 213 counts the number of the nematodes of which the final positional coordinate x1 is more than +α shown in FIG. 9 (x1>+α; that is, in an area 331 shown in FIG. 9). The number of the nematodes counted here is taken as N1 which is the number of nematodes demonstrating positive taxis (that is, an attraction action to the standard substance).

(D3) Next, the taxis index calculation section 213 counts the number of the nematodes of which the final positional coordinate x1 is less than −α shown in FIG. 9 (x1<−α; that is, in an area 332 shown in FIG. 9). The number of the nematodes counted here is taken as N2 which is the number of nematodes demonstrating negative taxis (that is, a repelling action to the standard substance).

(D4) Subsequently, the taxis index calculation section 213 counts the nematodes of which the final positional coordinate x1 is not less than −α and not more than +α shown in FIG. 9 (−α≤x1≤+α; that is, in an area 333 shown in FIG. 9). The number of the nematodes counted here is taken as N3 which is the number of nematodes demonstrating neutral taxis.

(D5)

Then, the taxis index calculation section 213 calculates the taxis index CI by the following expression (1) based on the number of the nematodes demonstrating attraction actions, N1, and the number of the nematodes demonstrating repelling actions, N2.

$$CI = (N1 - N2)/(N1 + N2) \quad (1)$$

Incidentally, the nematodes are counted, for example, by the following procedure. Incidentally, this procedure can also be applied for the processing of Step S204.

(E1) The image processing section 211 highlights the contrast in the image for test assay.

(E2) The image processing section 211 deletes the contour line of the taxis plate P and the medium from the image. This processing may be achieved in a manner that a tester selects the points corresponding to the taxis plate P and the medium in the image with a mouse or the like and then the image processing section 211 deletes the image on the selected points. Alternatively, since the positions of the taxis plate P and the medium are the same in all images, the points to be deleted in an image may be set in advance to allow the image processing section 211 to delete the points. The image processing section 211 changes the deleted points and the original background to black. Incidentally, the medium may be colored (desirably in a color close to black). This can make nematodes distinct without any processing (E2).

(E3) As the result of the processing of (E2), the nematodes are indicated as white grains against the black background.

(E4) The taxis index calculation section 213 sets the x-axis and the y-axis at the vertical and horizontal centers of the image. Furthermore, the taxis index calculation section 213 sets lines of +α and −α as shown in FIG. 9 in the image. Since the taxis plates P are imaged in the same size and direction, the taxis index calculation section 213 can easily set the x-axis, the y-axis, and the lines of +α and −α based on the information input in advance.

(E5) The taxis index calculation section 213 counts nematodes indicated as white grains to thereby confirm the final positional coordinates of the nematodes, and counts the nematodes existing beyond the line of +α, the nematodes existing beyond the line of −α, and the nematodes existing between the line of +α and the line of −α in FIG. 9.

Incidentally, the method for counting nematodes shown in (E1) to (E5) is one example, and another method may be used.

The description is now returned to FIG. 8 again.

Subsequently, the test determination processing section 215 determines whether or not the taxis index CI calculated in Step S213 is more than the predetermined threshold, 0 (CI>0) (S221).

When the taxis index CI is more than the predetermined threshold, 0, as a result of Step S221 (S221→Yes), the test determination processing section 215 determines the result of the cancer test to be positive (S222), and allows the processing to proceed to Step S231.

When the taxis index CI is equal to or less than the predetermined threshold, 0, as a result of Step S221 (S221→No), the test determination processing section 215 determines the result of the cancer test to be negative (S223), and allows the processing to proceed to Step S231.

In Step S231, the test determination processing section 215 stores the determination result of Step S222 or Step S223 in the storage device 203. Specifically, the test determination processing section 215 stores the determination result of Step S222 or Step S223 into the cancer test data 231 (see FIG. 2) of the storage device 203.

Then, the output processing section 216 prints (outputs) a cancer test result notification or the like via the output device 206 (S232).

On the other hand, when the culture condition of the nematodes or the taxis condition of the cancer test does not meet a predetermined condition or the mobility M is less than the predetermined threshold as a result of Step S206 (Step S206→No), the nematodes used are determined not to meet the quality condition.

Then, the quality determination processing section 215 instructs the control apparatus 3 to stop the test of the corresponding specimen (S241).

The control apparatus 3 which is instructed from the quality determination processing section 214 to stop the test stops the cancer test of the corresponding specimen in the cancer test apparatus 1 (S242), and the control apparatus 3 allows the display apparatus 4 to indicate the stop of the cancer test (S243).

Incidentally, Step S202 in FIG. 8 corresponds to Step S104 in FIG. 5, Steps S203 to S211 in FIG. 8 correspond to Step S105 in FIG. 5, Step S212 in FIG. 8 corresponds to Step S106 in FIG. 5, and Step S213 to S223 in FIG. 8 correspond to Step S107 in FIG. 5.

Incidentally, in this embodiment, the quality is considered to be "acceptable" in the case where the taxis/culture conditions meet predetermined conditions and in addition, the mobility is equal to or more than a predetermined threshold, but the quality determination may be made only by the mobility. In this case, Step S202 and S205 in FIG. 8 are omitted, and the quality determination processing section 214 determines whether or not the mobility M is equal to or more than a predetermined threshold in Step S206.

Cancer Test Data

FIG. 10 shows an example of cancer test data according to the first embodiment.

The cancer test data 231 includes the respective columns of test ID, culture condition, taxis condition, culture/taxis conditions determination result, mobility M (mm), mobility determination result, quality comprehensive result, taxis index CI, and cancer test result.

The specimen ID is ID for identifying the specimen used in the cancer test, which is uniquely added to the taxis plate P.

The culture condition is information about the environment where the nematodes are cultured, which includes the environmental temperature (° C.), the inoculum/*E. coli* 50 μL, and the medium composition.

The environmental temperature is the temperature in the environment where the nematodes are cultured.

The inoculum /*E. coli* 50 μL is the number of *E. coli* organisms seeded on the culture plate as feed of the nematodes. The numerical value indicates a result obtained by plotting 50 μL of a buffer containing *E. coli* and measuring the optical density with a turbidimeter. The optical density is measured at 600 nm.

The medium composition is information about the composition of the medium in the environmental plate. Incidentally, in FIG. 10, "B1" is stored in the medium composition in the culture condition, but it is symbolized for the simplification and specific numerical values, substance names, and the like are actually stored.

The taxis condition is a condition of the environment where the nematodes are allowed to undergo taxis actions, and includes the environmental temperature, medium composition, taxis time (minutes), and number of nematodes.

The environmental temperature is a temperature in the environment where the nematodes are allowed to undergo taxis actions.

The medium composition is information about the composition of the medium in the taxis plate P. Incidentally, in FIG. 10, "B2" is stored in the medium composition in the taxis condition, but it is symbolized for the simplification and specific numerical values, substance names, and the like are actually stored.

The taxis time is a time during which the nematodes are allowed to undergo taxis actions.

The number of nematodes is a number of the nematodes scattered in the taxis plate P.

The culture/taxis conditions determination result is a determination result of whether or not the culture condition and the taxis condition meet predetermined conditions (see Step S203 in FIG. 8). Specifically, determined is, for example, whether or not all or at least one of the environmental temperature in the culture condition and the environmental temperature and the number of nematodes in the taxis condition, which are variable elements, meet predetermined conditions. For example, determined is whether or not the condition of the environmental temperature in the culture condition falls within the range of 20±0.5° C. As for the condition of environmental temperature in the taxis condition, determined is whether or not the temperature falls within the range of 23±0.5° C. Furthermore, as for the condition of the number of nematodes, determined is whether or not the number is, for example, 20 or more.

The mobility M is a mobility calculated in Step S204 in FIG. 8, that is, an average of the distances that the nematodes in the taxis plate P have moved during a few minutes (2 minutes in this embodiment) from the start of the taxis actions of the nematodes.

The mobility determination result is a determination result of Step S206 in FIG. 8. In the example of FIG. 10, in the case of mobility M>6 (mm), the nematodes for the specimen IDs "P1" to "P4" meet the quality condition. That is, such a result indicates that the cancer test result by the nematodes of the corresponding taxis plate P is highly reliable. Incidentally, in the example of FIG. 8, the nematodes are considered to meet the quality condition in the case of mobility M>6 (mm), but the threshold is not limited to 6 mm.

The example of FIG. 10 shows that the nematodes for the specimen IDs of "P1" to "P4" meet the quality condition and the nematodes for the specimen ID of "P5" does not meet the quality condition.

The quality comprehensive result indicates whether or not the quality of the nematodes used in the cancer test of the corresponding specimen meets a predetermined condition. Here, the predetermined condition is whether or not all of the culture condition, the taxis condition, and the mobility M meet predetermined conditions. That is, when both of the culture/taxis conditions determination result and the mobility determination result are "pass", the "pass" is stored in the column of the quality comprehensive result. Either one of the culture/taxis conditions determination result and the mobility determination result is "fail", the "fail" is stored in the column of the quality comprehensive result.

Incidentally, in the specimen ID "P5", the determination result is "fail", in other words, the nematodes used do not meet the quality condition, and therefore the corresponding cancer test result is "stop".

Thus, when the determination of the quality assay is performed according to whether or not all of the culture condition, the taxis condition, and the mobility M meet predetermined conditions, it is possible to perform an assay in which the culture condition and the taxis condition are taken into account, enhancing the reliability in the quality assay.

The taxis index CI is the taxis index calculated in Step S213 in FIG. 8. The test determination processing section 215 performs the determination of the positivity or negativity of a cancer in the subject according to whether or not the taxis index exceeds a predetermined value.

The cancer test result is a result of a cancer test determined based on the taxis index CI. The "P" indicates "positive", and the "N" indicates the negative. Here, in the case of taxis index>0, the test determination processing section 215 makes determination of "positive", and in the case of taxis index CI≤0, the test determination processing section 215 makes determination of "negative". Incidentally, in the column of the cancer test result, "fail" indicates that the quality comprehensive result is "fail". That is, as a result of the first quality assay, the quality of the nematodes used has low reliability and thus the corresponding taxis index CI has low reliability so that the cancer test is stopped.

Incidentally, in the example of FIG. 10, specific values are stored in columns of the environmental temperature, the inoculum/*E. coli* 50 μL, and the medium composition in the culture condition, and the environmental temperature, the medium composition, and the taxis time in the taxis condition, but the present invention is not limited thereto, and the ID linked to another data may be stored. For example, medium condition data storing detailed information about the medium composition (not shown) may be separately stored in the storage device 203 and ID for linking to the medium condition data may be stored in the column of medium composition of the cancer test data.

The determination of quality assurance is performed here using the culture/taxis conditions determination result and the mobility determination result, but the determination of quality assurance may be made using only the mobility determination result as described above. In this case, the columns of the culture/taxis conditions determination result and the quality comprehensive result can be omitted.

Incidentally, in the cancer test data 231, the column of specimen ID, the columns in the culture condition, and the columns in the taxis condition are information that a tester inputs via the input device 205. In addition, the columns of mobility M and mobility determination result are information stored at the stage of Step S204 in FIG. 8.

The column of culture/taxis conditions determination result is information stored in the stage of Step S203 in FIG. 8.

In addition, the column of quality comprehensive result is information stored at the stage of Step S206 in FIG. 8.

The column of taxis index CI is information stored at the stage of Step S213 in FIG. 8. The column of cancer test result is information stored at the stage of Step S222 and Step S223 in FIG. 8.

Test Process

FIG. 11 shows an example of the detailed procedure for the cancer test according to the first embodiment. (a) shows a culture process and (b) shows a cancer test process.

As shown in FIG. 11(a), first, a plate preparer prepares a culture plate (S301). Then, the plate preparer performs a nematode subculture operation as needed (S311) to prepare a new culture plate (S312). Furthermore, the plate preparer performs a nematode subculture operation based on the culture plate prepared in Step S311 (S321) to prepare a new culture plate (S322).

Then, after nematodes are cultured in the culture plates prepared in Steps S301, S312, and S322, a tester performs the cancer test using the cultured nematodes (S341 to S343).

As shown in FIG. 11(b), in the cancer test, first, a plate preparer prepares the taxis plate P (S401).

Next, a tester plots sodium azide for paralyzing the nematodes on the taxis plate P prepared by the plate preparer (S402).

Next, the tester plots a specimen on the taxis plate P (S403).

Subsequently, the tester plots the nematodes on the taxis plate P (S404).

Then, the tester diffuses the nematodes plotted on the taxis plate P as shown in FIG. 9 (S405), and sets the taxis plate P in the cancer test apparatus 1 (S411).

Then, the camera for quality assay 101 in the cancer test apparatus 1 performs the imaging for quality assay in which the camera images the taxis plate P for approximately 2 minutes (S412). The imaging for quality assay here is the imaging for first quality assay. This processing is the processing of Step S202 in FIG. 8. Incidentally, the imaging time here is not limited to 2 minutes as long as an image required for the first quality assay can be obtained. The captured image (image for first quality assay) is sent to the analysis apparatus 2.

When the imaging in Step S412 is completed, the taxis plate P is allowed to stand still in the storage chamber 121 for approximately 13 minutes while the analysis apparatus 2 performs a quality assay processing using the image for first quality assay (S413). The quality assay processing here is the first quality assay processing. This processing is the same as the processing of Steps S203 to S211 in FIG. 8, and hence the detailed explanation is omitted here.

Then, the camera for test assay 111 in the cancer test apparatus 1 performs the imaging for test assay in which the camera images the taxis plate P for approximately 5 seconds (S414). This processing is the processing of Step S212 in FIG. 8. Incidentally, the imaging time here is not limited to 5 seconds as long as an image required for the test assay can be obtained. The captured image (image for test assay) is sent to the analysis apparatus 2.

The analysis apparatus 2 performs the test assay processing using the image for test assay captured in Step S414 (S415). Since this processing is the same as the processing of Steps S213 to S223 in FIG. 8, the detailed explanation is omitted here.

Then, the analysis apparatus 2 stores the processing result of Step S415 in the storage device 203 (S416).

In addition, the method for plotting urine or nematodes is not limited to the method of FIG. 9, and, for example, it is possible that the nematodes are plotted at the center of the taxis plate P (see FIG. 9) while the urine is plotted on a concentric circle of the taxis plate P. Alternatively, the following method may be employed: the nematodes are scattered on the taxis plate P and the urine is plotted at a predetermined position so that how many nematodes gather to the plotting position of the urine is observed.

FIG. 12 shows an example of the processes for the cancer test of Comparative Example. (a) shows a culture process, and (b) shows a cancer test process.

Incidentally, in FIG. 12, the same signals are put to the respective same treatments as in FIG. 11 and the explanation is omitted.

The process in FIG. 12(b) is different from the process in FIG. 11 in that the taxis plate is allowed to stand still for 1 hour (S413a) after being set in the cancer test apparatus 1 (S411) and then the camera for test assay 111 images the nematode during 30 minutes (S414a). After that, the same processing as in Step S415 and S416 in FIG. 11(b) is performed.

Hereinunder, with reference to FIG. 13 to FIG. 15, a result of an actual experiment using nematodes is shown. Incidentally, in FIG. 13 to FIG. 15, the method shown in FIG. 9 is used for plotting the nematodes and specimen.

Image for First Quality Assay

FIG. 13 shows an example of the image for first quality assay of nematodes according to the first embodiment. (a) shows an example where the movements of nematodes are not good and (b) shows an example where the movements of nematodes are good.

The image for first quality assay shown in FIG. 13 is captured in Step S102 in FIG. 8. That is, the image for first quality assay shown in FIG. 13 is obtained by continuously imaging the nematodes for 2 minutes from the start of taxis actions and recording the trajectories of the moving nematodes.

Incidentally, the method for plotting nematodes and the specimen is the method shown in FIG. 9.

It can be seen from the image for first quality assay shown in FIG. 13(a) that the nematodes do not significantly move from the central part of the taxis plate (circle).

In contrast, in the image for first quality assay shown in FIG. 13(b), it can be seen that the nematodes actively move.

The mobility calculation section 212 calculates the mobility by the above-mentioned methods of (C1) to (C4) based on the trajectories (black lines) as shown in FIG. 13(a) or FIG. 13(b).

Relationship between Plotting Condition and Mobility

FIG. 14 shows a relationship between the plotting condition and the mobility according to the first embodiment. Incidentally, the mobility in FIG. 14 and FIG. 15 is the mobility calculated by the above-mentioned method (C4).

In FIG. 14, the vertical axis shows the mobility (mm) and the horizontal axis shows the elapsed time (seconds) from the start of the taxis actions.

Here, the plotting condition is a condition when nematodes are plotted, and it is, for example, whether nematodes are plotted in a careful (or skillful) manner or in a rough (or rude) manner. In FIG. 14, the graph 401 shows a result of plotting nematodes in a careful manner, and the graph 403 shows a result of plotting nematodes purposely in a rough manner. The graph 402 shows a result of plotting nematodes with a level of care intermediate between the graph 401 and the graph 403.

As is clear from FIG. 14, the mobility of nematodes during 120 seconds (2 minutes) from the start of the taxis actions obviously correlates with the plotting condition. That is, the nematodes plotted in a careful manner (graph 401) show high mobility whereas the nematodes plotted purposely in a rough manner (graph 403) show low mobility. The graph 402 shows the mobility of a level intermediate between the graph 401 and graph 403.

Mobility and Relationship to Taxis Index

FIG. 15 shows a relationship between the mobility and the taxis index according to the first embodiment.

Here, the bar graph shows the taxis index and the solid line 501 shows the mobility during 2 minutes from the start of the taxis actions. In addition, the "good condition" in FIG. 15 shows the same plotting condition as in the graph 401 of FIG. 14, the "normal condition" shows the same plotting condition as in the graph 402 of FIG. 14, and the "bad condition" shows the same plotting condition as in the graph 403 of FIG. 14.

As shown in FIG. 15, when the plotting condition is good, the taxis index is high, and when the plotting condition is not good, the taxis index is low.

Thus, the inventors have found that, in a cancer test using nematodes, the activity (mobility, velocity, etc.) of the nematodes during the initial 1 to 2 minutes from the start of taxis actions correlates strongly with the taxis index. That is, the inventors have found the following: when the actions of the nematodes are active, the assay (the taxis index obtained) can be determined to be reliable, and in the other hand, when the actions of the nematodes are not active, the assay (the taxis index obtained) can be determined to be unreliable.

In addition, in the case of a cancer test using nematodes, a hundred-percent test is desirable due partly to a large individual variability of nematodes. According to the method for assessing a cancer test in the first embodiment, since the quality assay is performed on all the specimens to be subjected to the cancer test, a hundred-percent test is possible. Since a hundred-percent test is desirable in the case of a test using an organism such as nematodes as described above, the cancer test according to the first embodiment is highly effective.

In addition, whether or not nematodes can show an adequate cancer test result is associated with various factors including the state of the medium, the medium environment, the taxis environment, and the like as well as the skill of the tester as mentioned above. According to the first embodiment, however, the nematode quality can be assayed with the factors taken into account.

Incidentally, in the cancer test apparatus 1 in the first embodiment, one each of the camera for quality assay 101 and the camera for test assay 111 is provided. However, the invention is not limited thereto and it is possible that two or more each thereof are provided so that the imaging for quality assay and the imaging for test assay can be performed simultaneously on multiple specimens.

In addition, the camera for quality assay 101 and the camera for test assay 111 are preferably fixed. Furthermore, the camera for quality assay 101 and the camera for test assay 111 are preferably automatically focused.

The light source for quality assay 103 and the light source for test assay 113 can desirably adjust the quantity of light.

In this embodiment, the cancer test system 10 performs the quality assay (the first quality assay) in the imaging during 2 minutes from the start of the taxis actions, and then newly performs the test assay. However, the invention is not limited thereto and the cancer test system 10 may also perform the test assay by the imaging during 2 minutes from the start of the taxis actions.

In this embodiment, once the taxis plate P is placed on the imaging stage for quality assay 102, the imaging for first quality assay is started. However, the imaging for first quality assay may be started with the time at which a lid of the taxis plate P (petri dish) is closed as a trigger. In this case, the weight detection device may be provided in the imaging stage for quality assay 102 (see FIG. 3 and FIG. 4) and the control apparatus 3 may instruct the cancer test apparatus 1 to perform the imaging for first quality assay when the weight of the lid of the dish is added to the weight of the substance placed on the imaging stage for quality assay 102.

It is possible that a mark is put on a position where a specimen is plotted or a position where a nematode is plotted on the dish or medium of the taxis plate P and the mobility calculation section 212 and the taxis index calculation section 213 define the x-axis and y-axis on the taxis plate P based on the mark.

In this embodiment, the first quality assay is performed based on the mobility which is an average moving distance of the nematodes during 2 minutes from the start of the taxis actions. However, the first quality assay and the test assay may be performed based on the mobility and the taxis index during 2 minutes from the start of the taxis actions.

In addition, the order of the first quality assay and the test assay may be reversed.

The analysis apparatus 2 performs the first quality assay based on the mobility of the nematodes during 2 minutes from the start of the taxis actions in this embodiment, but the time period is not limited to 2 minutes from the start of the taxis actions as long as it is a time during which the mobility required for the first quality assay is obtained. The first quality assay may be performed based on the mobility until the taxis actions of the nematodes are completed.

In addition, the medium in the taxis plate P may be colored with a color that transmits light but is close to black. In this way, the analysis apparatus 2 can easily identify the nematodes.

Second Embodiment

Cancer Test System

FIG. 16 shows a configuration example of a cancer test system according to the second embodiment.

In a cancer test system K10 according to the second embodiment, in addition to the quality assay according to the first embodiment, a quality assay is performed by subjecting nematodes to a taxis assay using a standard substance, such as isoamyl alcohol, in place of urine. Incidentally, the quality assay in the second embodiment is referred to as second quality assay in order to distinguish it from the first quality assay in the first embodiment.

Here, the standard substance is a substance for which it is known whether nematodes undergo attraction actions or repelling actions (that is, it is known which taxis actions nematodes undergo), and in the second embodiment, isoamyl alcohol, for which it is known that nematodes undergo attraction actions, is used. Incidentally, in the second embodiment, isoamyl alcohol is used as a standard substance in the second quality assay, but the present invention is not limited thereto and the standard substance may be any chemical for which it is known whether nematodes undergo attraction actions or repelling actions.

In the second quality assay in the second embodiment, in addition to the quality assay according to the first embodiment, whether or not nematodes used in the cancer test are adequate is determined by analyzing taxis characteristics of the nematodes to isoamyl alcohol. Since it is known that nematodes undergo attraction actions to isoamyl alcohol, a quality of nematodes can be confirmed by assaying the attraction actions of nematodes to isoamyl alcohol.

The cancer test system K10 includes a quality assay apparatus K1, a quality analysis apparatus K2, the cancer test apparatus 1, and the analysis apparatus 2.

First, nematodes are dispensed from one culture plate (petri dish) Pa into five plates Pb to Pf (a plurality of assay units). Among the five plates Pb to Pf in which the nematodes are dispensed, four plates Pb to Pe (nematodes) are introduced into the cancer test apparatus 1 for a test assay. Accordingly, as for the plates Pb to Pe, the first quality assay is followed by the test assay.

In addition, one plate Pf (nematodes) is introduced into the quality assay apparatus K1 for the second quality assay. Incidentally, the nematodes are dispensed from one culture plate Pa into five plates Pb to Pf and four plates Pb to Pe among the five plates Pb to Pf are the plates for the test assay here, but the present invention is not limited to this configuration. Incidentally, the plates Pb to Pe for test assay are referred to as the taxis plates P as appropriate. In other words, the quality (activity such as freshness) of the nematodes used for the cancer test can be confirmed by dividing nematodes cultured in the same condition into those for test assay and those for second quality assay.

In the plate Pf, the nematodes and sodium azide are plotted as shown in FIG. 9, but in the areas 311 and 312 in FIG. 9, isoamyl alcohol which is a standard substance is plotted in place of the urine.

In addition, a specimen (urine) from the same subject is plotted in the plates Pb to Pe here, but specimens from different subjects may be plotted.

The quality assay apparatus K1 performs the second quality assay, and sends the obtained result to the quality analysis apparatus K2.

The quality analysis apparatus K2 analyzes the information about the quality of the nematodes used in the test based on the information obtained from the quality assay apparatus K1.

The cancer test apparatus 1 and the analysis apparatus 2 are the same devices as shown in FIG. 2.

The quality analysis apparatus K2 or the analysis apparatus 2 outputs a test result notification K900 to be given to the subject in which the test result is described.

Incidentally, in FIG. 16, a control apparatus for controlling the cancer test apparatus 1 or the quality assay apparatus K1 and sending a result obtained by the cancer test apparatus 1 or the quality assay apparatus K1 to the analysis apparatus 2 or the quality analysis apparatus K2 is not shown (omitted). In FIG. 16, the display apparatus 4 shown in FIG. 1 is not shown (omitted).

Quality Assay Apparatus

FIG. 17 is a functional block diagram showing a configuration example of the quality assay apparatus according to the second embodiment.

The quality assay apparatus K1 includes an imaging section K101, a placement section K102, and an illumination section K103.

On the placement section K102, the plate Pf (see FIG. 16) on which nematodes to be subjected to the second quality assay are dispensed is placed by a tester.

The illumination section K103 illuminates the plate Pf placed on the placement section K102 from below. The illumination section K103 is desirably an LED light source as with the light source for quality assay 103 and the light source for test assay 113 in the first embodiment.

The imaging section K101 images (captures an image of) the plate Pf (nematodes) placed on the placement section K102 and illuminated from below by the illumination section K103. Incidentally, in the second embodiment, the imaging section K101 is assumed to be a camera imaging a still image, but may be a video camera capturing a movie. Incidentally, the imaging section K101 desirably captures an image through auto-focusing.

Incidentally, a specific configuration example of the quality assay apparatus K1 will be described later.

Quality Analysis Apparatus

FIG. 18 is a functional block diagram showing a configuration example of the quality analysis apparatus according to the second embodiment.

The quality analysis apparatus K2 is, for example, a PC or the like, and includes a memory K201, a storage device K202, a CPU 203, a communication device K204, an input device K205, and an output device K206.

The communication device K204 sends data to and receives data from the quality assay apparatus K1 or the like.

The input device K205 is a key board, a mouse, or the like.

The output device K206 is a printer or the like in the second embodiment and prints the test result notification K900 (FIG. 16).

The storage device K202 is an HD, an SSD, or the like and stores quality assay data K24, nematode data K25, and the like. The quality assay data K24 and the nematode data K25 will be described later.

In the memory K201, a program stored in the storage device K202 is loaded, and the loaded program is executed by a CPU K203, whereby a counting section K211, a calculating section K212, a determination section K213, an output processing section K214 are embodied.

The counting section K211 counts the number of nematodes demonstrating attraction actions to the standard substance (isoamyl alcohol), the number of nematodes demonstrating repelling actions to the standard substance, or the number of nematodes demonstrating neutral actions. Here, the neutral action is an action of a nematode demonstrating neither of the attraction action and the repelling action.

The calculating section K212 calculates the taxis index CI based on the counting result by the counting section K211. The taxis index will be described later.

The determination section K213 performs quality determination of whether or not the nematodes used in the cancer test are adequate based on the taxis index CI calculated by the calculating section K212.

The output processing section K214 prints the determination result given by the determination section K213 on the test result notification K900.

Incidentally, since the configurations of the cancer test apparatus 1 and the analysis apparatus 2 were described in FIG. 2 to FIG. 4, description is omitted here.

Incidentally, the quality assay apparatus K1 and the cancer test apparatus 1 are different devices here, but the devices may be integrated into one device. Similarly, the quality analysis apparatus K2 and the analysis apparatus 2 are different devices here, but may be integrated into one device.

Specific Configuration of Quality Assay Apparatus

FIG. 19 and FIG. 20 are diagrams showing an example of a specific configuration of the quality assay apparatus according to the second embodiment. FIG. 19 shows a state before nematodes are set, and FIG. 20 shows a state after the plate Pf is set. Incidentally, the quality assay apparatus K1 shown in FIG. 19 and FIG. 20 is one example and the present invention is not limited to this configuration.

First, as shown in FIG. 19, the plate Pf is placed on the plate-shaped placement section K102. Then, when the placement section K102 is pushed into the device by a tester, the placement section K102 slides along a sliding section K111 and is set on the glass section K112 (FIG. 19) (see FIG. 20). Incidentally, in the placement section K102, the part below the level at which the plate Pf is set is composed of a transparent member.

As shown in FIG. 19, the glass section K112 is composed of a transparent member. The illumination section K103 (see FIG. 17) is placed below the glass section K112. When the placement section K102 is set on the glass section K112 as shown in FIG. 20, the illumination section K103 is turned on and illuminates the plate Pf from below. Incidentally, the turning-on of the illumination section K103 may be achieved by a tester through operation of a lighting switch provided in the quality assay apparatus K1. Alternatively, for example, a switch or sensor may be provided at an end of the sliding section K111 so that the illumination section K103 is turned on in response to setting of the placement section K102 on the glass section K112.

As shown in FIG. 19, the placement section K102 is joined to a base K113, and the base K113 is joined to a first supporting section K114 of an annular shape. Then, a second supporting section K115 having a rod shape is supported in a form of being inserted in an annular portion of the first supporting section K114. A clamping section K116 is provided around the end of the second supporting section K115 opposite to the end at which the first supporting section K114 is provided. The clamping section K116 is attached on the second supporting section K115 by a clamping force of screws K121. The clamping section K116 is provided with a third supporting section K117 having an L-shape, for example, by a screw (not shown) or the like, and the third supporting section K117 is provided with an imaging section K101 at the end opposite to the joint with the second supporting section K115.

The imaging section K101 is provided so as to face the glass section K112, and when the placement section K102 is set on the glass section K112 and the illumination section K103 is turned on, the imaging section K101 images the plate Pf (nematode). The imaging may be performed by a tester through operation of a switch provided on the quality assay apparatus K1, or the imaging may be automatically performed upon the turning-on of the illumination section K103.

Incidentally, when the screws K121 in the clamping section K116 are loosened, the clamping section K116 becomes able to move along the second supporting section K115. By this operation, the height of the imaging section K101 can be adjusted.

Incidentally, a tester places the plate Pf on the placement section K102 in the state of FIG. 19 and sets the placement section K102 on the glass section K112 as shown in FIG. 20, and then the tester images the plate Pf (nematode) by the imaging section K101. Subsequently, the tester draws the placement section K102 to thereby return the device back to the state of FIG. 19, and then takes out the plate Pf. Then, the tester places another plate Pf on the placement section K102 and performs imaging in the same manner. In addition, the tester places again the plate Pf in which a predetermined time elapses after the imaging on the placement section K102 and images the plate in the same procedure. By repeating the operation, images of the nematodes captured at constant intervals can be obtained.

Data Configuration

Next, with reference to FIG. 21 to FIG. 22, various data stored in the storage devices K202 and 402 are explained. In FIG. 21 to FIG. 22, FIG. 16 will be referred to as needed.

Incidentally, in the second embodiment, the record of the test data 231 in FIG. 10 are desirably provided for each taxis plate P. For example, it is desirable that each of the four taxis plates P dispensed from the same culture plate Pa is provided with a record of the test data 231.

Quality Assay Data

FIG. 21 shows a configuration example of the quality assay data according to the second embodiment.

The quality assay data K24 includes columns of the plate ID, taxis temperature (° C.), taxis time (minutes), illumination condition, nematode group ID, nematode total number, positive taxis, negative taxis, neutral, taxis index CI, standard substance, and acceptable line.

The plate ID is the ID for the plate Pf.

The taxis temperature is a temperature when the nematodes are allowed to undergo taxis actions in the second quality assay.

The taxis time is a time during which the nematodes are allowed to undergo taxis actions in the second quality assay.

The illumination condition is the brightness of the illumination section K103 (FIG. 17) in the second quality assay. Incidentally, in the example of FIG. 21, the illumination section K103 is always in the turned-on state. However, the illumination section K103 may be in the turned-off state during the nematodes are allowed to undergo taxis actions as with the case of FIG. 22 and the illumination section K103 may be turned on when the imaging is performed.

The nematode group ID is an ID for linking to information in the nematode data K25 described later. That is, the quality assay data K24 is linked to the nematode data K25 by the nematode group ID.

The nematode total number is a total number of the nematodes used in the second quality assay (dispersed in the plate Pf).

The positive taxis is the number of nematodes demonstrating attraction actions to isoamyl alcohol.

The negative taxis is the number of nematodes demonstrating repelling actions to isoamyl alcohol.

In the neutral, the number of the nematodes demonstrating neither of the attraction action and the repelling action to isoamyl alcohol is stored.

In the taxis index CI, an index regarding the taxis actions of the nematodes calculated by a predetermined technique described later is stored.

Incidentally, the positive taxis, the negative taxis, the neutral, and the taxis index will be explained later.

The standard substance is a substance used in place of the urine in the test assay, and isoamyl alcohol is used here.

The acceptable line is an acceptable line on a result of the second quality assay, and in the second embodiment, the case where the taxis index CI is equal to or more than "+0.7" as a result of the second quality assay using isoamyl alcohol as a standard substance is taken as acceptable.

In the example of FIG. 21, the plate IDs "Pf1" and "Pf2" are acceptable and the plate ID "Pf3" is not acceptable.

Incidentally, a taxis condition in quality assurance taxis is the same taxis condition as for the taxis plates P dispensed from the same culture plate Pa.

Incidentally, in the quality assay data K24, the respective information pieces of the plate ID, taxis temperature, taxis time, illumination condition, nematode group ID, standard substance, and acceptable line are input by a manager or a tester via the input device K205 (see FIG. 18). In addition, the information pieces of the nematode total number, positive taxis, negative taxis, neutral, and taxis index CI are stored by the second quality assay processing described later.

Incidentally, in the quality assay data K24, the columns for culture condition and taxis condition may be provided as with the case of the test data 231 shown in FIG. 10.

Nematode Data

FIG. 22 shows configuration example of the nematode data according to the second embodiment.

The nematode data K25 are data for managing information on a nematode individual, and includes columns of the nematode group ID, individual ID, time (seconds after), Feret diameter (mm), coordinate, moving distance (mm), velocity (mm/s), average Feret diameter (mm), average moving distance (mm), and average velocity (mm/s).

The nematode group ID is information for identifying a nematode group used in the second quality assay. Incidentally, as described above in FIG. 21, the quality assay data K24 and the nematode data K25 are linked to each other by a nematode group ID.

The individual ID is an ID imparted to each individual of the nematodes in a nematode group identified by a nematode group ID.

The time is an elapsed time during which the nematode is allowed to undergo taxis actions in the second quality assay.

The Feret diameter is a size shown in FIG. 23. The reason why the Feret diameter is used is that it is difficult to accurately measure the body length (straightened length) of a nematode K701 which is always moving. The Feret diameter is a size as shown in FIG. 23, and thus varies depending on the degree of elongation of the nematode. Incidentally, the Feret diameter is not limited to the size shown in FIG. 23, and may be defined by the diagonal line of the rectangle shown in FIG. 23, a major axis of an approximated ellipse, or the like. Here, the ellipse is, for example, the ellipse that is inscribed to the rectangle shown in FIG. 23.

The coordinate shows the position of the nematode in the corresponding elapsed time. As for the x-coordinate and the y-coordinate here, as shown in FIG. 9, with the center of the plate Pf taken as an origin, a direction of a position K801 where isoamyl alcohol is plotted (described later in detail) is defined as the positive x-coordinate, and the y-coordinate is defined to be perpendicular to the defined x-coordinate in the plane of the plate Pf.

The moving distance is a moving distance of the nematode in the corresponding elapsed time.

The velocity is a velocity of the nematode in the corresponding elapsed time. The velocity is calculated as (moving distance)/(elapsed time).

The average Feret diameter is the average of Feret diameters of nematodes in a nematode group represented by a nematode group ID.

The average moving distance is the average of moving distances of nematodes in a nematode group represented by a nematode group ID.

The average moving velocity is the average of moving velocities of nematodes in a nematode group represented by a nematode group ID.

Incidentally, in the nematode data K25, the nematode group ID and the individual ID are information input by a manager or a tester via the input device K205 (see FIG. 18). Other information is information calculated and input by the counting section K211 (see FIG. 18) and the like.

Flowchart

FIG. 24 is a flow chart showing a procedure of a second quality assay processing according to the second embodiment. FIG. 17 to FIG. 20 will be appropriately referred.

First, the counting section K211 identifies the positions of nematodes after migration (final positional coordinates) (SK101). At this time, the counting section K211 inputs the result of counting into the column of the nematode total number in the quality assay data K24 shown in FIG. 21.

Then, the counting section K211 counts the nematodes of which the final positional coordinate x1 is more than $+\alpha$ shown in FIG. 9 (x1>$+\alpha$; that is, in the area 331 shown in FIG. 9) (SK102). Taking the number of the nematodes counted here as N1 which is the number of nematodes demonstrating positive taxis (that is, an attraction action to the standard substance), the counting section K211 inputs the result of the counting into the column of positive taxis in the quality assay data K24 shown in FIG. 21.

Next, the counting section K211 counts the nematodes of which the final positional coordinate x1 is less than $-\alpha$ shown in FIG. 9 (x1<$-\alpha$; that is, in the area 332 shown in FIG. 9) (SK103). Taking the number of the nematodes counted here as N2 which is the number of nematodes demonstrating negative taxis (that is, a repelling action to the standard substance), the counting section K211 inputs the result of the counting into the column of negative taxis in the quality assay data K24 shown in FIG. 21.

Subsequently, the counting section K211 counts the nematodes of which the final positional coordinate x1 is not less than $-\alpha$ and not more than $+\alpha$ shown in FIG. 9 ($-\alpha \leq x1 \leq +\alpha$; that is, in the area 333 shown in FIG. 9) (SK104). Taking the number of nematodes counted here as N3 which is the number of nematodes demonstrating neutral taxis, the counting section K211 inputs the result of the counting into the column of neutral in the quality assay data K24 shown in FIG. 21. At this time, the counting section K211 may calculate N1+N2+N3 and store the value into the column of nematode number in the quality assay data K24 shown in FIG. 21.

The procedure for counting nematodes was explained in Step S213 of FIG. 8, and hence the explanation is omitted here.

After Step SK104, on the basis of the counting results of the counting section K211, the calculating section K212 calculates a taxis index CI (SK105). The taxis index CI is calculated by the formula (1) mentioned above.

Next, the determination section K213 determines whether or not the taxis index CI calculated in Step SK105 is more than a predetermined value $\beta$ (corresponding to the acceptable line in FIG. 21) (CI>$\beta$) (SK106).

When the taxis index CI is more than the predetermined value $\beta$ (SK106→Yes) as a result of Step SK106, the determination section K213 determines the nematodes to have no problem (SK107). That is, the determination section K213 determines that a cancer test using nematodes dispensed from the same lot as the nematodes subjected to the assay has high reliability.

When the taxis index CI is equal to or less than the predetermined value $\beta$ (SK106→No) as a result of Step SK106, the determination section K213 determines the nematodes to have a problem (SK108). That is, the determination section K213 determines that a cancer test using nematodes dispensed from the same lot as the nematodes subjected to the assay has low reliability.

When the result is determined to have a problem in Step SK108, the tester retries a cancer test by using a nematode lot other than the lot that was subjected to the assay. This enables a cancer test with high reliability.

Then, the output processing section K214 writes the determination results of Step SK107 and Step SK108 into the test result notification K900.

Test Result Notification

FIG. 25 shows an example of the test result notification according to the second embodiment.

The test result notification K900 is for indicating results of the quality assay and the test assay in the first embodiment or the second embodiment to the subject, and includes a test result area K901 and a quality assurance area K902.

In the test result area K901, a cancer test result by nematodes (a result of a cancer test by the analysis apparatus 2) is printed. Incidentally, the cancer test result is printed with reference to the column of cancer test result of FIG. 10.

In the quality assurance area K902, a result of a quality assay by the analysis apparatus 2 or the quality analysis apparatus K2 is printed. That is, the fact is printed that the nematodes used in the cancer test have a secured quality. The inclusion of the quality assurance area K902 as described above can enhance the reliability of the subject.

In addition to the result of the quality assay, information about the criteria on which the quality assay was conducted may be printed in the quality assurance area K902. This can enhance the reliability of the subject in the cancer test.

The cancer test system K10 according to the second embodiment dispenses nematodes into a plurality of plates Pb to Pf from the same culture plate Pa, and nematodes in the plates Pb to Pe are used for the first quality assay and the test assay and nematodes in the plate Pf are used in the second quality assay. In this way, in addition to the effect of the cancer test system 10 according to the first embodiment, the cancer test system K10 according to the second embodiment can assay the nematode quality of the same culture condition as for the nematodes (nematode group) used in the cancer test, and can easily confirm whether or not the nematodes used in the cancer test is in an adequate condition for the test.

In addition, the cancer test system K10 according to the second embodiment can further enhance the quality assurance by using the same taxis condition both in the test assay and the second quality assay.

An actual cancer test uses a plurality of plates. That is, urine, sodium azide for paralyzing nematodes, and nematodes are plotted plural times.

As a result, information is required about what state of nematodes was used and what operation was conducted for the result of the cancer test, in other words, about whether the state of nematodes used was adequate for the cancer test.

In the second embodiment, by allowing the same tester to conduct the second quality assay and the test assay, it can be easily determined whether the result in the cancer test conducted by the tester is reasonable or not.

In the second quality assay of the second embodiment, the quality assurance is determined based on the attraction actions or the repelling actions of nematodes. More specifically, the quality assurance is determined based on the taxis index CI according to the formula (1). In this way, according to the second embodiment, in addition to the effect of the first embodiment, the quality assurance can be determined in a quantified manner and the reliability in the quality assurance can be enhanced.

In the second embodiment, the quality assay apparatus K1 includes the imaging section K101, and the attraction actions or the repelling actions of nematodes in the plate Pf are assayed on the basis of an image captured by the imaging section K101 (imaging result information). In this way, according to the second embodiment, in addition to the effect of the first embodiment, the taxis action of nematodes can be assayed after being subjected to image processing.

In addition, the second embodiment uses a standard substance for which it is previously known whether nematodes perform attraction actions or repelling actions (what taxis actions the nematodes perform). Thus, according to the second embodiment, in addition to the effect of the first embodiment, it can be further confirmed what state (activity, or the like) the nematodes have. Especially, when isoamyl alcohol to which nematodes show strong attraction actions is used, the state (activity or the like) of the nematodes can be significantly shown.

Furthermore, by showing to the subject the test result notification K900 in which information about quality assurance is put together with the cancer test result, according to the second embodiment, in addition to the effect of the first embodiment, the reliability of the subject in the cancer test can be enhanced.

In this way, according to the second embodiment, in addition to the effect of the first embodiment, the quality assurance for nematodes having high reliability can further be performed.

Especially, the first quality assay in the first embodiment can determine whether the tester procedure is good or bad and the second quality assay in the second embodiment can determine whether or not the culture condition and the taxis condition for the nematodes are truly good so that the cancer test reliability can be considerably enhanced.

In addition, when the nematode quality assay is conducted as in the first embodiment and second embodiment, it is possible to control whether or not the nematodes used in sequential subcultures are a wild type, that is, whether or not any mutation and the like inadequate to the cancer test is caused.

The determination in the quality assurance is binarized into "having a problem" and "having no problem" in the first embodiment and the second embodiment. The present invention is however not limited thereto, and the determination can be indicated in a multi-valued manner with multiple ranks.

In addition, the test result notification K900 is printed on paper in the first embodiment and the second embodiment. The present invention is however not limited thereto, and the notification may be displayed on a screen of a given PC or the like through a log-in processing by the subject.

The urine as a specimen used in the test assay is desirably filtered through a sterilizing filter or a filter for removing impurities.

Urine is used as a specimen for use in the test assay in the first embodiment and the second embodiment, but a bio-related material originating in a subject, such as sweat, cells, blood, saliva, and exhalation of the subject, may be used.

Wild-type nematodes are assumed to be used in the first embodiment and the second embodiment. However, genetically modified nematodes, such as those obtained by allowing an olfactory nerve of the nematodes to express an indicator gene that enabling measurement of the intraneural calcium concentration, may be used (transgenic nematodes may be used or knockout nematodes in which a certain gene is deleted by disruption may be used).

Urine (or standard substance)+sodium azide is plotted on the areas 311 and 312 in FIG. 9 and sodium azide is plotted on the areas 321 and 322 in FIG. 9 in the first embodiment and the second embodiment, but the present invention is not limited thereto. For example, urine (or standard substance)+sodium azide may be concentrically plotted on the periphery of the medium.

Nematodes used in the first quality assay and the second quality assay are plotted at the center (the area 301) of the plate P (Pf) in FIG. 9 in the first embodiment and the second embodiment, but the present invention is not limited thereto as long as the taxis actions of the nematodes can be measured at the position. For example, the nematodes may be scattered on the medium on the plate P (Pf) so that how many nematodes gather around the urine (or standard substance)+sodium azide is measured.

The cancer test system 10 and K10 obtained in the first embodiment and the second embodiment may be placed at a test center so that a test kit is sent to a subject from the test center. Then, the subject may enclose a specimen (urine) in the test kit and then send the test kit to the test center so that the test center conducts the cancer test in the first embodiment and the second embodiment with the specimen in the test kit sent above.

Incidentally, the present invention is not limited to the above-mentioned embodiments, and encompasses various modifications. For example, the above-mentioned embodiments are described in detail for explaining the present invention in an easy-to-understand manner, and the present invention is not necessarily limited to an embodiment having all the configurations described herein. In addition, a part of configurations of one embodiment may be substituted by a configuration of another embodiment, or a configuration of one embodiment may be added to configurations of another embodiment. In addition, in a part of configurations of each embodiment, another configuration may be added, deleted, or substituted.

A part or all of the above-mentioned configurations, functions, sections 211 to 216 and K211 to K214, the storage devices 203 and K202, and the like may be realized by means of a hardware, for example, by designing them with an integrated circuit. As shown in FIG. 2 and FIG. 18, the above-mentioned configurations, functions, and the like may be realized by means of a software by allowing a processor, such as the CPUs 202 and K203, to understand and execute programs for realizing the respective functions thereof. Information, such as programs, tables, and files, for realizing the respective functions may be stored in an HD as shown in FIG. 2 and FIG. 18 as well as in a storage device, such as a memory and SSD, or in a recording medium, such as an integrated circuit (IC) card, a secure digital (SD) card, and a digital versatile disc (DVD).

Control lines and information lines that are considered to be required for explanation are shown in the embodiments, and all the control lines and information lines for a product are not always shown. Almost the all configurations may be considered to be actually connected to each other.

REFERENCE SIGNS LIST

1: cancer test apparatus
2: analysis apparatus
3: control apparatus
4: display apparatus
10, K10: cancer test system
101: camera for quality assay (quality information acquisition section, imaging section)
102: imaging stage for quality assay (imaging stage)
103: light source for quality assay
111: camera for test assay (test information acquisition section)
112: imaging stage for test assay
113: light source for test assay
121: storage chamber
122: discard chamber
131: movement device
141: plate placement stage
142: temperature control device
211: image processing section
212: mobility calculation section (first taxis information generation section)
213: taxis index calculation section (second taxis information generation section)
214: quality determination processing section (quality determination section)
215: test determination processing section (cancer test determination section)
216: output processing section
231: cancer test data
K1: quality assay apparatus
K2: quality analysis apparatus
K211: counting section
K212: calculation section
K213: determination section
K214: output processing section
K24: quality assay data
K25: nematode data
K101: imaging section
K102: placement section
K103: illumination section
K900: test result notification
K901: test result area
K902: quality assurance area
P: taxis plate
Pa: culture plate
Pb to Pf: plates

The invention claimed is:

1. A cancer test device comprising:
a first camera configured to capture a first image of nematodes on a taxis plate to assay a quality of the nematodes, urine from a subject being placed on the taxis plate;
a second camera configured to capture a second image of the nematodes on the taxis plate to determine a cancer in the subject;
a memory configured to store a program; and
a processor programmed to:
obtain a mobility of the nematodes by calculating an average distance of distances that the nematodes on the taxis plate have moved during an initial predetermined period of time based on the captured first image;
determine whether the mobility of the nematodes is more than a predetermined value;
determine whether a culture temperature at which the nematodes are cultured is within a first predetermined temperature range;
determine whether a taxis temperature at which the nematodes move on the taxis plate is within a second predetermined temperature range;
determine that the quality of the nematodes is acceptable when the processor determines that the mobility of the nematodes is more than the predetermined value, the culture temperature is within the first predetermined temperature range, and the taxis temperature is within the second predetermined temperature range; and determine a presence of the cancer in the subject when a taxis index of the nematodes from the captured second image is more than a predetermined threshold.

2. The cancer test device according to claim 1,
wherein, before the processor is programmed to cause the first camera to capture the first image, the nematodes are arranged on the taxis plate along a first direction, the urine is spaced apart from the nematodes along a second direction on the taxis plate, and the first direction is perpendicular to the second direction, the processor is programmed to obtain the mobility of the nematodes by calculating an average component distance of components along the second direction of the distances that the nematodes on the taxis plate have moved during the initial predetermined period of time based on the captured first image, and the average distance of the distances that the nematodes on the taxis plate have moved during the initial predetermined period of time corresponds to the average component distance of the components along the second direction of the distances.

3. The cancer test device according to claim 1,
wherein the processor is programmed to cause the second camera to capture the second image of the nematodes on the taxis plate after the processor obtains the mobility of the nematodes, and the initial predetermined period of time is in a range of 30 seconds to two minutes.

4. The cancer test device according to claim 1,
wherein the processor is programmed to detect a weight of the taxis plate that is placed on an imaging stage, and the processor is programmed to cause the first camera to capture the first image of the nematodes on the taxis plate when the processor detects a change in the weight.

5. The cancer test device according to claim 1,
wherein the processor is programmed to determine that the quality of the nematodes is acceptable when the processor determines that the mobility of the nematodes is more than 6 mm as the predetermined value and the taxis temperature is within 23° C.±0.5° C. as the second predetermined temperature range.

6. The cancer test device according to claim 5,
wherein the processor is programmed to determine that the quality of the nematodes is acceptable when the processor determines that the culture temperature is within 20° C.±0.5° C. as the first predetermined temperature range.

7. The cancer test device according to claim 1,
wherein the first camera is configured to capture a movie or time-lapse images as the first image, the processor is programmed to calculate a sum of the distances that the nematodes on the taxis plate have moved from an initial position to a current position for every frame of the movie or for every image of the time-lapse images during the initial predetermined period of time, and the processor is programmed to obtain the mobility of the nematodes by calculating a time average of the sum of the distances.

8. The cancer test device according to claim 1,
wherein the first camera is configured to capture a movie or time-lapse images as the first image, the processor is programmed to calculate a sum of the distances in a horizontal direction that the nematodes on the taxis plate have moved from an initial position to a current position for every frame of the movie or for every image of the time-lapse images during the initial predetermined period of time, and the processor is programmed to obtain the mobility of the nematodes by calculating a time average of the sum of the distances.

9. The cancer test device according to claim 1,
wherein the first camera is configured to continuously capture a plurality of static images as the first image, and the processor is programmed to obtain the mobility of the nematodes by calculating an average of a sum of a distance that each of the nematodes on the taxis plate has moved from an initial position to a current position for a fixed time during the initial predetermined period of time.

* * * * *